US012109176B1

(12) United States Patent
Bryan

(10) Patent No.: US 12,109,176 B1
(45) Date of Patent: *Oct. 8, 2024

(54) EFFECT OF GLYCEROL ON BIOFILM FORMING BACTERIA AND FUNGI THAT CHANGES THE MICROBES SENSITIVITY TO PRO AND ANTI-BIOFILM NON-TOXIC, NON-BONDED PLASMA AMINO ACIDS AND AMINO ACID DERIVATIVES

(71) Applicant: Thomas Bryan, Marina, CA (US)

(72) Inventor: Thomas Bryan, Marina, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,192

(22) Filed: Apr. 20, 2023

(51) Int. Cl.
*A61K 31/047* (2006.01)
*A61K 31/198* (2006.01)
*A61K 45/06* (2006.01)
*A61P 31/04* (2006.01)
*A61P 31/10* (2006.01)
*C02F 1/50* (2023.01)

(52) U.S. Cl.
CPC .......... *A61K 31/047* (2013.01); *A61K 31/198* (2013.01); *A61K 45/06* (2013.01); *A61P 31/04* (2018.01); *A61P 31/10* (2018.01); *C02F 1/50* (2013.01); *C02F 2303/04* (2013.01)

(58) Field of Classification Search
CPC .... A61K 31/047; A61K 31/198; A61K 45/06; A61P 31/04; A61P 31/10; C02F 1/50; C02F 2303/04
See application file for complete search history.

(56) References Cited

U.S. PATENT DOCUMENTS

| | | |
|---|---|---|
| 2,887,380 A | 5/1959 | Driscoll et al. |
| 3,328,259 A | 6/1967 | Anderson |
| 4,826,680 A | 5/1989 | Nachf |
| 5,112,810 A | 5/1992 | Mitsui |
| 5,156,973 A | 10/1992 | Shanbrom |
| 5,711,937 A | 1/1998 | Nisjida et al. |
| 5,811,446 A | 9/1998 | Cytos |
| 5,872,127 A | 2/1999 | Cincotta et al. |
| 6,103,748 A | 8/2000 | Bryan |
| 6,274,612 B1 | 8/2001 | Bryan |
| 7,906,544 B2 | 3/2011 | Melander et al. |
| 8,241,611 B2 | 8/2012 | Dashper et al. |
| 8,420,673 B2 | 4/2013 | Pasteris et al. |
| 8,425,932 B2 | 4/2013 | Wryer et al. |
| 9,480,669 B2 | 11/2016 | Bryan et al. |
| 9,549,904 B2 | 1/2017 | Bryan |
| 2011/0046041 A1 | 2/2011 | Neesham-Grenon et al. |
| 2011/0236453 A1 | 9/2011 | Stensen et al. |
| 2012/0315260 A1 | 12/2012 | Ivanova et al. |
| 2013/0059096 A1 | 3/2013 | Losick et al. |
| 2013/0123319 A1 | 5/2013 | Bryan |
| 2014/0018438 A1 | 1/2014 | Bryan |
| 2015/0126571 A1 | 1/2015 | Bryan |
| 2017/0042851 A1 | 2/2017 | Bryan et al. |
| 2018/0153840 A1 | 6/2018 | Bryan |
| 2022/0117924 A1 | 4/2022 | Bryan |

FOREIGN PATENT DOCUMENTS

| | | |
|---|---|---|
| AU | 760993 | 1/2000 |
| EP | 2521542 | 11/2012 |
| GB | 2514863 | 12/2014 |
| WO | 199965479 | 12/1999 |
| WO | 2011085326 | 7/2011 |
| WO | 2016112140 | 7/2016 |

OTHER PUBLICATIONS

Procalamine package insert (2008) (Year 2008).
Fitzpatrick, F. et al., "Evidence for icaADBC-independent biolfilm development mechanism in methicillin-resistant *Staphylococcus areus* clinical isolates," Journal of Clinical Microbiology, vol. 43, No. 4, pp. 1973-1976, Apr. 2005.
Mahmoud Abd et al, "N-acetylcysteine Inhibits and Eradicates Candida albicans Biofilms," American J. Infectious Diseases and Microbiology, 2014, vol. 2(5), pp. 122-130.
Helms, Steve and Miller, Alan L., "Natural Treatment of Chronic Rhinosinusitis," Alternative Medicine Review (2006), vol. 11(3), pp. 196-207.
PCT/US16/12395, Methods of destroying and preventing bacterial and fungal biofilm by amino acid infusion—International Search Report and Written Opinion—May 6, 2016.
Ponikau et al., Mayo Clinic Proceedings 1999, vol. 74(9), pp. 1-2. Intravenous Infusion of Bone Marrow in Patients Receving Radiation and Chemotherapy, http://www.osti.gov/energycitations/product.biblio.jsp?osti_id=4331366.

(Continued)

*Primary Examiner* — Savitha M Rao
*Assistant Examiner* — Andrew P Lee
(74) *Attorney, Agent, or Firm* — Concourse Law Group; Katherine B. Sales, Esq.

(57) ABSTRACT

A method of desensitizing microbes to pro-biofilm amino acids and amino acid derivatives in plasma comprising administering a sufficient amount of glycerol. A method of sensitizing microbes to anti-biofilm amino acids and amino acid derivatives in plasma comprising administering a sufficient amount of glycerol. Methods of increasing a plasma concentration of glycerol comprising administering a sufficient amount of glycerol. A method of treating an infection and/or contamination comprising applying glycerol and anti-biofilm amino acids and/or amino acid derivatives to a surface to be treated and/or water to be treated. A method of treating a biofilm producing viral infection comprising administering a sufficient, non-toxic concentration of glycerol. A method of treating a protozoal infection comprising administering a sufficient, non-toxic concentration of glycerol. A method of treating a hybrid infection comprising administering a sufficient, non-toxic concentration of glycerol and anti-biofilm amino acids and/or amino acid derivatives.

5 Claims, No Drawings

(56) References Cited

OTHER PUBLICATIONS

Suh, JD et al., "Biofilms in Chronic Rhinosinusitis." Current Opinion in Otolaryngology & Head & Neck Surgery., vol. 18, No. 1, 2010.

Non-Final Office Action in U.S. Appl. No. 17/565,024, dated Apr. 27, 2023.

EFFECT OF GLYCEROL ON BIOFILM FORMING BACTERIA AND FUNGI THAT CHANGES THE MICROBES SENSITIVITY TO PRO AND ANTI-BIOFILM NON-TOXIC, NON-BONDED PLASMA AMINO ACIDS AND AMINO ACID DERIVATIVES

CROSS-REFERENCE TO RELATED APPLICATIONS

This application is a continuation in part of U.S. patent application Ser. No. 18/160,559, titled "Methods for Treating Microbial Biofilms by the Use of Non-Toxic, Non-Bonded Amino Acids and Amino Acid Derivatives with or without the influence of Glycerol in Order to Influence Biofilm Formation and Maintenance by the Responsible Microbes," filed Jan. 27, 2023, the contents of which are incorporated by reference herein in their entirety.

FIELD OF THE INVENTION

The embodiments disclosed herein relate to methods and compositions that enable physiologic changes in biofilm-producing microbes that affect the formation and integrity of biofilm made by biofilm-forming microorganisms that cause infections and contaminations.

BACKGROUND

Biofilm producing microbes such as bacteria, fungi, and hybrids, the later consist of a shared biofilm combination of fungal and bacterial biofilm, protists and viral particles that cause infections that can instruct an infected cell to produce biofilm which enables the safe transfer of virus to uninfected cells, are a major cause of morbidity and mortality in humans and there is an urgent need for the development of new antibiofilm agents that can safely destroy their biofilm, as biofilm is the chief cause for difficult to treat chronic infections and microbial antibiotic.

Most urgently, biofilm is the major cause in the development of genetic resistance to antimicrobials. This genetic resistance, especially in pathologic bacteria that cause infections in animals including humans, has become common worldwide. The World Health Organization regards this as a major threat to the welfare of humanity.

Accordingly, there is a need for an improved method of treating and preventing microbial biofilm.

SUMMARY OF INVENTION

The present invention satisfies this need. In a first embodiment, the present invention is directed to a method of desensitizing microbes to pro-biofilm amino acids and amino acid derivatives in plasma comprising administering a solution comprising a sufficient, non-toxic concentration of glycerol.

Optionally, the step of administering comprises irrigating a wound with the solution.

Optionally, the step of administering comprises administering the solution vaginally, rectally, orally, intravenously, intracavernously, topically, intra-arterially, and intrathecally.

Optionally, 1.7 to 4.3 g/h of glycerol are administered intravenously and/or intra-arterially.

Optionally, the method further comprises the step of administering at least one antimicrobial.

In a second embodiment, the present invention is directed to a method of sensitizing microbes to anti-biofilm amino acids and amino acid derivatives in plasma comprising administering a solution comprising a sufficient, non-toxic concentration of glycerol.

Optionally, the step of administering comprises irrigating a wound with the solution.

Optionally, the step of administering comprises administering the solution vaginally, rectally, orally, intravenously, intracavernously, topically, intrathecally, and intra-arterially.

Optionally, 1.7 to 4.3 g/h of glycerol are administered intravenously and/or intra-arterially.

Optionally, the method further comprises the step of administering at least one antimicrobial.

In a third embodiment, the present invention is directed to a method of increasing a plasma concentration of glycerol comprising the step of administering a sufficient, non-toxic concentration of glycerol that will cause the infecting biofilm producing microbes to become insensitive to probiofilm amino acids and probiofilm amino acid derivatives and increase their sensitivity to anti-biofilm amino acids and anti-biofilm amino acid derivatives.

Optionally, the step of administering comprises irrigating a wound with the solution.

Optionally, the step of administering comprises administering the solution vaginally, rectally, orally, intravenously, intracavernously, topically, intrathecally, and intra-arterially.

Optionally, 1.7 to 4.3 g/h of glycerol are administered intravenously and/or intra-arterially.

Optionally, the method further comprises the step of administering at least one antimicrobial.

In a fourth embodiment, the present invention is directed to a method of treating an infection and/or contamination comprising the step of applying a composition comprising glycerol and anti-biofilm amino acids and/or anti-biofilm amino acid derivatives to a surface to be treated and/or water to be treated.

Optionally, the method further comprises the step of administering an antimicrobial.

Optionally, the method further comprises the step of administering at least one sterilizing agent.

In a fifth embodiment, the present invention is directed to a composition for desensitizing microbes to pro-biofilm amino acids and amino acid derivatives in plasma comprising a therapeutically effective amount of glycerol.

Optionally, the therapeutically effective amount of glycerol comprises 1.7 to 4.3 g/h of glycerol to be infused intravenously and/or intra-arterially.

In a sixth embodiment, the present invention is directed to a method of treating a biofilm producing viral infection comprising the step of administering a sufficient, non-toxic concentration of glycerol.

Optionally, the method further comprises the step of administering at least one antiviral agent.

In a seventh embodiment, the present invention is directed to a method of treating a protozoal infection comprising the step of administering a sufficient, non-toxic concentration of glycerol in order to effect a change in the infecting or contaminating protists in order to stop the protists from making their biofilm.

Optionally, the method further comprises the step of administering at least one anti-protozoal agent.

In an eighth embodiment, the present invention is directed to a method of treating a hybrid infection, the method comprising the step of administering a sufficient, non-toxic concentration of glycerol and one or more anti-biofilm amino acids and/or anti-biofilm amino acid derivatives to a site of an infecting hybrid infection.

Optionally, the method further comprises the step of administering at least one antimicrobial.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. Other embodiments of the invention will readily suggest themselves to such skilled persons having the benefit of this disclosure. In some instances, well-known features have not been described in detail so as not to obscure the invention.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used in this disclosure, the term "comprise" and variations of the term, such as "comprising" and "comprises," do not exclude other components or steps.

Unless otherwise defined, all technical and scientific terms used herein have the same meaning as commonly understood by one of ordinary skills in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The embodiments include a composition of glycerol in plasma in a sufficient concentration to cause a physiologic/pathologic change in the biofilm producing microbes that have direct contact with plasma amino acids and amino acid derivatives affected by the glycerol.

Also disclosed are compositions for the treatment of biofilm that is made by pathogenic biofilm-producing microbes that are not in contact with plasma amino acids or amino acid derivatives as for example, in or on the body of animals including humans such as on the skin and toenails, in or on a cyst or an abscess, in a body cavity, or inside the cranium or surrounding an organ.

Also disclosed are compositions for the reduction/removal of biofilm that is produced by biofilm-forming microbes that are infecting or contaminating plants, or contaminate inanimate surfaces such as in medical facilities, in food processing environments, in manufacturing facilities, in pipes that are used for the transport of water or other fluids and/or gases etc., which would enable sterilizing agents or antimicrobials to get better access to the offending microbes once the protection of the biofilm has been removed.

Additionally, the disclosure relates to pharmaceutical compositions for the treatment of biofilm that cause infections in areas of the body that do not have access to plasma amino acids or amino acid derivatives such as for example: on skin, on eyes, on external ear or middle ear infections, on nails, on/or/in infected cysts or abscesses, in infected sinuses, in cavities, or intracranially, comprising one or a plurality of non-bonded antibiofilm amino acids and/or amino acid derivatives and pharmaceutically acceptable salts thereof for treatment of fungal and bacterial infections characterized by biofilm formation. Also provided herein are the compositions, or pharmaceutical compositions for use in the treatment and prevention of a pathogenic biofilm producing fungal infection, bacterial infection, protozoal infection, and viral infection, and in the decontamination of surfaces and water by potentially pathogenic biofilm-forming microbes that cause infections in animals including humans. The composition may comprise non-bonded antibiofilm amino acids such as the non-bonded amino acid, aspartic acid, or a pharmaceutically acceptable salt thereof, at a weight to volume percent from about 0.001% to about 5.0%; non-bonded cysteine, or a pharmaceutically acceptable salt thereof, at a weight to volume percent from about 0.001% to about 5.0%; non-bonded glutamic acid, or a pharmaceutically acceptable salt thereof, at a weight to volume percent from 0.001% to about 5.0%. These compositions may include a concentration of glycerol that would increase the anti-biofilm potency of antibiofilm amino acids and antibiofilm amino acid derivatives effect on infecting or contaminating biofilm microbes. The composition or the pharmaceutical composition may comprise: non-bonded aspartic acid, or a pharmaceutically acceptable salt thereof, at a weight to volume percent from about 0.001% to about 5.0%, plus non-bonded cysteine, or a pharmaceutically acceptable salt thereof, at a weight to volume percent from about 0.001% to about 5.0%, plus non-bonded glutamic acid, or a pharmaceutically acceptable salt thereof, at a weight to volume percent from about 0.001% to about 5.0%, with or without an appropriate concentration of glycerol.

The disclosure also relates to pharmaceutical compositions for the treatment of biofilm-forming pathogenic or potentially pathogenic microbes that may respond to other non-bonded, non-toxic amino acid(s) and/or amino acid derivative(s). Some of these occur naturally in animals or plants. Others can be synthesized in the laboratory. They all must be aimed at biofilm-forming microbes. They must all be non-toxic or with an acceptable level of toxicity in the animal or plant that is being treated in order to successfully treat the infectious microbe and must not be responsible for damage to the environment that they or their manufacturing process may have exposure to.

The disclosure also relates to pharmaceutical compositions for aiding in the riddance of a nuisance biofilm-forming microbe from a surface such as in an industrial environment, in transportation, in industrial piping, or water piping etc., wherein the antibiofilm amino acids and the antibiofilm amino acid derivatives with/or without glycerol may be either nontoxic or toxic for animal consumption but otherwise not toxic to the environment.

The method of aiding plants in the treatment of infections caused by biofilm producing microbes by applying a composition of amino acids and/or amino acid derivatives with or without glycerol along with an anti-microbial and/or a sterilization agent.

Depending on the species, genus, order, or strain of microorganism being targeted for elimination the disclosure relates to the presence of a sufficient concentration of Glycerol in order to enhance the ability of antibiofilm amino acids and antibiofilm amino acid derivatives being used in the treatment of biofilm whose concentration at the site of infection may require a concentration from 0.002% to 0.004%, 0.004% to 0.006%, 0.006% to 0.01%, 0.0% to 0.03%, 0.03% to 0.05%, 0.05% to 0.075%, 0.075% to 0.1%, 0.1% to 0.3%, 0.3% to 0.5%, 0.5% to 0.7%, 0.7% to 1.0%, 1.0% to 1.25%, 1.25% to 1.5%, 1.5% to 2.0%, 2.0% to 2.5%, 2.5% to 3.0%, 3.0% to 3.5%, 3.5% to 4.0%, 4.0% to 5.0%, 5.0% to 10.0%, in order to be effective in the prevention and reduction of biofilm being made by the targeted microbe.

The disclosure also relates to the compositions, pharmaceutical compositions or formulations disclosed herein for use in aiding the treatment of a surface contaminated by biofilm-forming microorganisms. Some compositions are designed for the surface of an implantable device or a catheter or drain tube, or a shunt. Some compositions are designed as an aid in the sterilization of surfaces in hospitals and healthcare facilities. Some compositions are designed for application to the surface surrounding a live body organ, or onto skin, or onto an infected nail, or onto the surface of a burn, or onto the surface of a wound, or onto the inner surface of an ulcer, or onto the inner surface of an infected cyst or abscess, or in a cavity such as the pleural cavity or the abdominal cavity or the urinary bladder, or for the post-operative prevention of a biofilm producing bacterial infection. In some the composition is designed to be used on surfaces in a food processing facility. In some the purpose of the composition is for the treatment of a fungal infection that produces biofilm such as *Candida* species fungus, e.g., *C. albicans* and *C. aurius.*

In some embodiments of the methods described herein is for the purpose of treating a bacterial infection that produces biofilm. These may include one or a plurality of bacterial cells derived from or chosen from one or a plurality: *A. baumanni, A. ursingii, Streptococcus pneumoniae, Strep. epdermidis, Strep. suppurans, Strep. viridans, Bacillus* spp, *Listeria monocytogenes, Staphylococcus* spp, methicillin resistant Staph *aureus*, and lactic acid bacteria, including *Lactobacillus plantarum* and *Lactococcus lactis*, and/or *Streptococcus mutans, Pseudomonas aeruginosa, Enterococcus fecalis, E. coli, Klebsiella pneumonia, Proteus mirabilis*, etc. In some embodiments the contamination is caused by biofilm producing protozoans or viruses.

The disclosure also relates to the compositions, pharmaceutical compositions, or formulations disclosed herein as an aid to the treatment of water contaminated by biofilm producing microorganisms.

The disclosure also relates to the compositions, pharmaceutical compositions, or formulations disclosed herein as an aid to the treatment of disease caused by a virus that induces biofilm by the infected cell which enables the virus to infect an adjacent cell.

The term "active state" refers to the conformation or set of conformations of the amino acid to associate or dissociate with another compound, macromolecule, or ligand. In some embodiments, the association or dissociation of amino acids with another compound, macromolecule or ligand, may propagate or inhibit a biologic signal propagated by the microbial species colonizing or growing on a surface and/or in a subject.

The term "administering" or "administration" and the like refers to providing one or a plurality of compositions, including glycerol, to a subject in need of treatment so as to produce a sufficient concentration of glycerol in the subject's plasma to cause the necessary changes in the subjects plasma amino acids and amino acid derivatives to affect an increased antibiofilm effect in the subjects antibiofilm amino acids and antibiofilm amino derivatives and an attenuation of the pro-biofilm effect in the pro-biofilm amino acids and amino acid derivatives that will result in a decrease in biofilm formation and cause a decrease in already formed biofilm caused by the infecting biofilm-producing bacteria and/or fungus and/or protozoan and/or virus. Likewise, an amino acid and/or an amino acid derivative with antibiofilm effectiveness may be administered in order to increase the necessary antibiofilm effect needed to treat biofilm made by a particular microorganism. The subject is a mammal or a non-mammalian animal. The present disclosure also relates to administering one or a plurality of compositions of glycerol of the disclosure in conjunction with one or more antibiotics, such as a β-lactam antibiotic, or an anti-fungal agent. When one or a plurality of compositions of the disclosure are administered in conjunction with an antibiotic and/or an antifungal agent, and/or an antiprotozoal agent, and/or an antiviral agent, with glycerol, can be administered simultaneously in the same composition, simultaneously in different dosage forms or sequentially or at different times.

When the one or a plurality of compositions of glycerol and the antimicrobial are administered at the same time they can be administered as a single composition or a pharmaceutical composition or they can be administered as separate pharmaceutical compositions. It is understood that when one or a plurality of compositions of glycerol and an antimicrobial are administered in a single combination or in multiple combinations. For example, when administered intravenously, the one or a plurality of compositions or molecules of the disclosure can be dissolved or suspended in any of the commonly used intravenous fluids and administered by infusion, and then an antibiotic can be dissolved or suspended in any of the commonly used intravenous fluids and administered by infusion. Conversely, the antimicrobial can be dissolved or suspended in any of the commonly used intravenous fluids and administered by infusion, and then one or a plurality of compositions of glycerol of the disclosure can be dissolved or suspended in any of the commonly used intravenous fluids and administered by infusion. Alternatively, a pharmaceutical composition comprising one or a plurality of compositions of glycerol of the disclosure and an antimicrobial can be dissolved or suspended in any of the commonly used intravenous fluids and administered by infusion.

Alternatively, these compositions can be administered orally or via diffusion through a mucosal membrane, via an artery, or intrathecally to an animal, including humans.

Alternatively, these compositions can be administered individually or in any combination via the various means of administration depending on the appropriate or preferable way of administration of each by the administering clinician in charge of the administration. The term "amino acid" refers to a molecule containing both an amino group and a carboxyl group bound to a carbon which is designated an alpha-carbon. Amino acid also refers to or includes, without limitation, both the D- and L-isomers of the naturally-occurring amino acids, as well as non-naturally occurring amino acids prepared by organic synthesis or other metabolic routes. A single "amino acid" might have multiple sidechains moieties, as available per an extended aliphatic or aromatic backbone scaffold. These compositions comprise amino acids with non-natural side chains. Unless the context specifically indicates otherwise, the term amino acid, as used herein, is intended to include only L isomers or no isomer. Non-natural amino acids of the disclosure include only L-isomers or combinations of L-isomers. The compositions, pharmaceutical compositions, or decontamination solutions are free of D-isomers of any naturally occurring non-bonded amino acid or salts thereof. In some embodiments, the composition or pharmaceutical composition of the disclosure comprises a therapeutically effective amount of at least one non-bonded, non-toxic amino acid or an amino acid derivative or a pharmaceutically acceptable salt thereof. The amino acid or the amino acid derivative may be a non-bonded natural or non-natural amino acid or amino acid derivative or a pharmaceutically acceptable salt thereof. In the case of non-natural amino acids, the non-bonded amino acid or amino acid derivative or a salt thereof, may be modified with non-natural chemical substituents on its side chain and/or amino terminus and/or carboxy terminus. In some compositions, the non-bonded amino acid or amino acid derivative is an isomer or optical isomer of the natural amino acid or amino acid derivative from which it is derived.

As used herein, the term "derived from" in the context of the relationship between a chemical structure or amino acid sequence and a related chemical structure or related amino acid sequence describes a chemical structure or amino acid sequence that may be homologous to or structurally similar to the related chemical structure or related amino acid sequence. For instance, nor leucine is an amino acid derived from leucine because it comprises a chemical formula substantively based upon the chemical formula of leucine. The "derived from" molecule is regarded as being a primary, secondary, or a tertiary amine which is derived from a primary, secondary, or tertiary amino acid and may have facets of its structure that are quite different from its parent amino acid. There are a multitude of known amino acid derivatives that may be effective in aiding the reduction in the formation of biofilm and in the reduction of preformed biofilm by a specific biofilm-forming pathogenic microbe that is causing an infection in animals or plants or causing interference with the distribution of piped water or other liquids and gases.

As used herein "a therapeutically effective amount" refers to an amount of a compound, material, or composition, as described herein, that is effective in achieving a particular biological result such as, but not limited to, biological results disclosed, described, or exemplified herein. Such results may include but are not limited to, the effective reduction of signs and symptoms associated with any bacterial, fungal, protozoan, or viral infection of the disease states mentioned herein, as determined by any means suitable in the art. Such results may include, but are not limited to, the effective disruption of bacterial biofilm growth or maintenance, the effective disruption of fungal biofilm growth or maintenance, the effective disruption of protozoan biofilm growth or maintenance, or the effective disruption of viral-induced biofilm growth or maintenance or the reduction of clinically relevant numbers of bacterial, fungal, or protozoan cells or viral particles at or proximate to the surface of an implanted or non-implanted medical device or surface intended to be sterile or found on/or in any surface that is causing an infection. The effective amount of the composition may be dependent on any number of variables, including, without limitation, the species, breed, size, height, weight, age, the overall health of the subject, the type of formulation, the mode or manner of administration, the type and/or severity of the particular condition being treated, or the need to modulate the activity of the molecular pathway induced by association of the analog to its receptor or in regards to any induced adverse effect on the subject being treated. The appropriate effective amount can be routinely determined by those of skill in the art using routine optimization techniques and the skilled and informed judgment of the practitioner and other factors evident to those skilled in the art. The appropriate therapeutic amount may need to be changed depending on an ill effect on organs such as blood, kidney, liver, heart, muscles, nerves, brain, and the immune system. A therapeutically effective amount of the compositions or pharmaceutical compositions described herein may provide a partial or complete cure or resolution of signs and symptoms associated with the bacterial, fungal, protozoan, or viral infections of the subject being treated as compared to the signs and symptoms or infection of subjects who are left untreated. A therapeutically effective dose of the glycerol described herein may provide a sustained biochemical or biological effect and/or an increased vulnerability of bacterial, fungal, protozoan, and viral infections to treatment by interfering with biofilm formation and reduction of already formed biofilm when a composition includes glycerol is administered to a subject as compared to the same subject were it left untreated.

The embodiment also includes an increase in the plasma concentration of a certain non-bonded amino acid or amino acids and/or one or more non-bonded amino acid derivative in order to treat the biofilm of certain microbes that require a higher concentration of any of these molecules in order to treat the biofilm that is made by any of these microbes.

The term "non-bonded" amino acid or amino acid derivative encompasses a single amino acid or an amino acid derivative or pharmaceutically acceptable salt thereof with a free amino or carboxyl group not covalently bound to another molecule or chemical substance. The composition, pharmaceutical composition or decontamination solution of the disclosure comprises a naturally occurring amino acid or an amino acid derivative or a non-naturally occurring amino acid or an amino acid derivative in a solid dosage form or liquid dosage form that is not covalently bound to a molecule or chemical substance. The compositions, pharmaceutical compositions or decontamination solution of the disclosure comprises a non-bonded amino acid salt or a non-bonded salt of an amino acid derivative which may be complexed with a buffer, salt or other small chemical compound, but the amino acid is not integrated within a polypeptide. The composition, pharmaceutical composition or decontamination solution of the present disclosure comprises one or more amino acids and/or amino acid derivatives that are bound to a chemical group or substituent that when administered to a surface or a subject and exposed to a pharmacologically active substance (environmentally available or physiologically available in a subject) is cleaved to form a free amino acid or an amino acid derivative not covalently bound to a component of the composition, pharmaceutical composition or decontamination solution. This form would be considered a pro-drug form of the amino acid or an amino acid derivative. "Non-bonded" forms of the claimed amino acids or amino acid derivatives include those pro-drug forms that may or may not have a cleavable substituent that, under therapeutically effective conditions, are cleaved from the amino acid or amino acid derivatives in the composition.

A "non-natural side chain" is a modified or synthetic chain of atoms joined by a covalent bond to the α-carbon atom, β-carbon atom, or γ-carbon atom which does not make up the backbone of the polypeptide chain of amino acids. The non-natural side chain of the composition may be a methyl group in which one or more of the hydrogen atoms is replaced by a deuterium atom.

The term "polypeptide" encompasses two or more naturally, or non-naturally occurring amino acids joined by a covalent bond (e.g., an amide bond). Polypeptides, as described herein, include full-length proteins (e.g., fully processed pro-proteins or full-length synthetic polypeptides) as well as shorter amino acid sequences (e.g., fragments of naturally-occurring proteins or synthetic polypeptide fragments) that comprise or are free of carbohydrate modifications.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable, although salts of non-pharmaceutically acceptable acids may be of utility in the preparation and purification of the compound in question. Salts of the embodiments include those formed from hydrochloric, hydrobromic, sulfuric, phosphoric, citric, tartaric, lactic, pyruvic, acetic, succinic, fumaric, maleic, methane sulphonic and benzene sulphonic acids.

In some embodiments salts of the compositions comprising one or many may be formed by reacting the free base, or a salt, enantiomer, or racemate thereof, with one or more equivalents of the appropriate acid. In some embodiments, pharmaceutically acceptable salts of the present invention refer to amino acids having at least one basic group or at least one basic radical. Pharmaceutically acceptable salts of the present invention comprise a free amino group, a free guanidino group, a pyridinyl radical, or a pyridyl radical that forms acid addition salts. The pharmaceutically acceptable salts of the present invention refer to amino acids that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxy maleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid, additional salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze-drying. The reaction may also be a metathetical process, or it may be carried out on an ion exchange resin. The salts may be those that are physiologically tolerated by a patient. Salts, according to the present invention, may be found in their anhydrous form or as in hydrated crystalline form (i.e., complexed or crystallized with one or more molecules of water).

The term "soluble" or "water soluble" refers to solubility that is higher than $1/100,000$ (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is $1/10,000$ (mg/ml) or less. Water soluble or soluble substances include, for example, polyethylene glycol. In some embodiments, the modified or natural amino acid of the claimed invention may be bound by polyethylene glycol to better solubilize the composition comprising the peptide of the amino acid.

The term "subject" is used throughout the specification to describe an animal or plant to whom treatment with the compositions according to the present invention is provided or administered. For treatment of those conditions which are specific for a specific subject, such as a human being, the term "patient" may be interchangeably used. In some instances, in the description of the present invention, the term "patient" will refer to human patients. In some embodiments, the subject may be a mammal to whom the present invention is provided or administered. In some instances, the subject may be a non-mammalian animal to whom the present invention is provided or administered. In some instances, the subject is a mammal, as in a canine, equine, feline, porcine, bovine, murine, caprine, ovine, or other domesticated mammals. In some instances, the subject is human, and in some instances, the subject is a non-mammalian animal such as a bird or another vertebrate. In some instances, the animal is an invertebrate.

The terms "treating" and "to treat", mean to alleviate signs and/or symptoms, eliminate the causation either on a temporary or permanent basis, or to prevent or slow the appearance of signs and symptoms. The term "treatment" includes alleviation, elimination of causation (temporary or permanent) of, or prevention of signs and/or symptoms and disorders associated with any condition caused by a biofilm producing microorganism, such as a fungal infection, bacterial infection, protozoan infection, or a viral infection that causes disease or discoloration. The treatment may be a pre-treatment (as a preventative treatment) and/or treatment at the onset of signs and/or symptoms.

As used herein, the term "transmucosal delivery" refers to the delivery of a pharmaceutical agent across a mucous membrane in the oral cavity, pharyngeal cavity, distal rectum, and the vagina, and may be contrasted, for example, with traditional oral delivery, in which absorption of the drug occurs in the intestines where it then travels via the portal system to the liver where some or all of it may be metabolized.

TABLE A

Pharmaceutical Compositions Comprising Amino Acids and/or Glycerol

| Indwelling medical device | Organisms |
| --- | --- |
| Central venous catheter | Coagulase-negative staphylococci, *Staphylococcus aureus*, *Enterococcus faecalis*, *Klebsiella pneumoniae*, *Pseudomonas aeruginosa*, *Candida albicans* |
| Prosthetic heart valve | *Viridans Streptococcus*, coagulase-negative staphylococci, entercocci, *Staphylococcus aureus* |
| Urinary catheter | *Staphylococcus epidermidis*, *Escherichia coli*, *Klebiella pneumoniae*, *Enterococcus faecalis*, *Proteus mirabilis* |
| Artificial hip prosthesis | Coagulase-negative staphylococci, β-hemolytic streptococci, enterococci, *Proteus mirabilis*, *Bacterioides* species, *Staphylococcus aureus*, viridans *Streptococcus*, *Escherichia coli*, *Pseudomonas aeruginosa* |
| Artificial voice prosthesis | *Candida albicans*, *Streptococcus mitis*, *Streptococcus salivarius*, *Rothia dentrocariosa*, *Candida tropicalis*, *Streptococcus sobrinus*, *Staphylococcus epidermidis*, *Stomatococcus mucilaginous* |

An object of the disclosure is a pharmaceutical composition comprising one or a plurality of non-bonded amino acids and/or non-bonded amino acid derivatives and/or glycerol or glycerol alone in a therapeutically effective amount. In some compositions, the non-bonded amino acid and/or amino acid derivative of the composition may be in a liquid dosage form but dissolved at a concentration of from about 0.001% to about 10% weight per volume. In some, compositions the non-bonded amino acid(s) or amino acid derivative(s) of the composition, without or with glycerol, may be in a liquid dosage form but dissolved at a concentration of from about 0.001% to about 10% weight per volume, wherein the composition is free of any one or plurality of non-bonded pro-biofilm amino acids from Table D.

In some embodiments, the term to be "free of" the non-bonded amino acid or an amino acid derivative in the composition may refer to be free of an amount sufficient to cause a deleterious effect on the inhibition and/or reduction in the treatment of biofilm such that the addition of that amount encourages formation of or stability of a bacterial or fungal biofilm. In some embodiments, to be "free of" a particular amino acid means that the composition or pharmaceutical composition disclosed herein is free of a percentage weight to volume of one or a plurality of pro-biofilm non-bonded amino acids or amino acid derivatives or salts thereof equal to no greater than about 0.001%, 0.01% 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0%, in trace amounts or at a concentration that would not affect the biological effect of an effective amount of one or more amino acids that have a disruptive or inhibitory effect on the bacterial and/or fungal biofilm formation or maintenance. To be "free of" a particular amino acid or an amino acid derivative means that the composition or pharmaceutical composition disclosed herein is free of a particular percentage weight to volume of one or a plurality of non-bonded pro-biofilm amino acids and salts thereof identified in Table D For instance, the composition or pharmaceutical compositions comprise a first non-bonded amino acid or a first non-bonded amino acid derivative and is "free of" the second or more non-bonded amino acids or the derivatives of amino acids. The composition or pharmaceutical composition disclosed herein, wherein the second or more non-bonded amino acid or an amino acid derivative, is not present at an independently discrete concentration or range, such as about 0.001%, 0.01, 0.02%, 0.03%, 0.04%, 0.05%, 0.06%, 0.07%, 0.08%, 0.09%, 0.10%, 0.11%, 0.15%, 0.2%, 0.25%, 0.30%, 0.035%, 0.40%, 0.45%, 0.50%, 0.55%, 0.60%, 0.65%, 0.70%, 0.75%, 0.80%, 0.85%, 0.90%, 0.95%, or about 1.0% In some embodiments, the composition or pharmaceutical composition is free of one or a plurality of non-bonded amino acids or non-bonded amino acid derivative(s) at a concentration of X nM, wherein X is any positive integer from about 1 to about 10,000. Any range of from about 1 to about any positive integer to about 10,000 is contemplated by the embodiment.

In some embodiments, the pharmaceutical composition or formulation disclosed herein comprises a range of any one or plurality of one or plurality of disclosed non-bonded amino acids or amino acid derivatives from about 0.001% to about 0.39% in weight to volume of solution. In some embodiments, the pharmaceutical composition or formulation disclosed herein comprises a range of any one or plurality of one or plurality of disclosed non-bonded amino acids or amino acid derivatives from about 0.39% to about 5.0% in weight to volume of solution.

In some embodiments a pharmaceutical composition or formulation comprising non-bonded amino acids or non-bonded amino acid derivatives of the disclosure or salts thereof, and optionally further comprising an antimicrobial agent with or without glycerol for the treatment of biofilm.

In some compositions, the pharmaceutical compositions or formulations comprise aspartic acid, or salts thereof, optionally, further comprising an antimicrobial agent with or without glycerol. In some compositions, the pharmaceutical compositions or formulations comprise cysteine, or salts thereof, optionally, further comprising an antibiotic or anti-fungal agent with or without glycerol. In some embodiments, the pharmaceutical compositions or formulations comprise glutamic acid, or salts thereof, optionally further comprising an antibiotic or anti-fungal agent with or without glycerol. In some others, the pharmaceutical compositions or formulations comprise antibiofilm amino acids and amino acid derivatives disclosed herein, or salts thereof, optionally further comprising an antimicrobial, with or without glycerol or comprising an antimicrobial with glycerol without comprising amino acids or amino acid derivatives. In some compositions, the pharmaceutical compositions or formulations comprise cysteine, or salts thereof plus aspartic acid, or salts thereof plus glutamic acid or a salt thereof. In some of the pharmaceutical compositions or formulations comprise one or more of the antibiofilm amino acids and/or the antibiofilm amino acid derivatives comprising cystathionine, homocysteine, hydroxyproline, lysine, phosphoethanolamine, proline, and valine or salts thereof, optionally further comprising an antibiotic or anti-fungal agent and glycerol.

For prophylactic treatment of diseases and the treatment of diseases caused by bacterial infections, fungal infections, protozoan infections, and viral infections or for treatment of bacterial cells, fungal cells, protozoan cells, or viral particles that are in a biofilm state or benefit from a biofilm state. Some of the pharmaceutical compositions are formulated for administration topically, irrigation of wounds either as wound dressing or in sterile solution, intradermally, on skin, on and in mucus membranes, intravenously, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, swish and swallow treatment of oral candidiasis, on nails, or for transmucosal or transdermal delivery.

The pharmaceutical preparations disclosed herein may be prepared in accordance with standard procedures and are administered at dosages that are selected to reduce, prevent or eliminate biofilm formation or maintenance (see, e.g., Remington's Pharmaceutical Sciences, Mack Publishing Company, Easton, Pa. and Goodman and Gilman's "The Pharmaceutical Basis of Therapeutics," Pergamon Press, New York, N.Y, the contents of which are incorporated herein by reference, for a general description of the methods for administering various antimicrobial agents for human therapy).

The pharmaceutical compositions can comprise one or more of the compounds disclosed herein (e.g. one or more amino acid and/or amino acid derivative compositions), optionally further comprising a second composition such as an antibiotic or antifungal agent or an antiprotozoan agent or an antiviral agent and glycerol, in association with one or more non-toxic pharmaceutically-acceptable carriers and/or diluents and/or adjuvants and/or excipients. As used herein, the phrase "pharmaceutically acceptable carrier" refers to any and all solvents, dispersion media, coatings, antibacterial, antifungal, antiprotozoan, and antiviral agents, isotonic and absorption delaying agents, and the like, that are compatible with pharmaceutical administration. The use of such media and agents for pharmaceutically active substances is well known in the art. Non-limiting examples of carriers and excipients include cornstarch or gelatin, lactose, sucrose, microcrystalline cellulose, kaolin, mannitol, dicalcium phosphate, and sodium chloride. The compositions may contain croscarmellose sodium, microcrystalline cellulose, corn starch, sodium starch glycolate and alginic acid.

Dosage forms may comprise tablet binders, lubricants and or flavoring agents. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention (e.g. amino acid compositions), in conjunction with an antimicrobial agent and glycerol can be mixed with conventional pharmaceutical carriers and excipients and used in the form of tablets, capsules, elixirs, suspensions, syrups, wafers and the like. The compositions comprising a compound of this invention may contain from about 0.001% to about 99% by weight of the active compound, such as from about 10% to about 30%. In some embodiments, the compositions are free of cysteine or a salt thereof at 0.5% weight to volume in a liquid solution. In some embodiments, the compositions are free of aspartic acid at 0.5% weight or a salt thereof to volume in a liquid solution.

In some embodiments, the compositions are free of glutamic acid or a salt thereof at 0.5% weight to volume in a liquid solution. In some embodiments all three of the amino acids, Aspartic acid, Cysteine, and Glutamic acid are present in combination. For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical composition may be made in the form of a dosage unit containing a therapeutically effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Non-limiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition (e.g. amino acid and amino acid derivative compositions) optionally in conjunction with an antimicrobial agent and glycerol can be dissolved or suspended in any of the commonly used intravenous fluids and administered by infusion. Intravenous fluids include, without limitation, physiological saline or Ringer's solution. Intravenous administration may be accomplished by using, without limitation, syringe, mini-pump or intravenous line.

For access of glycerol to the systemic circulation, the glycerol can be placed in the vagina and/or the distal rectum and/or the oral cavity where it can get absorbed through the mucus membrane into the systemic circulation thus avoiding a first pass through the liver where it can be metabolized.

Pharmaceutical compositions of this disclosure (e.g. amino acids, amino acid derivatives, and glycerol compositions) for parenteral injection comprise pharmaceutically-acceptable aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use or storage.

Solid dosage forms for oral administration include capsules, tablets, pills, powders, and granules. Such forms may include forms that dissolve or disintegrate quickly in the oral environment. In such solid dosage forms, the active compound preferably a non-bonded cysteine (optionally with or without a non-bonded aspartic acid and/or a non-bonded glutamic acid) can be mixed with at least one inert, pharmaceutically acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof, and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. No. 4,452,775 (issued to Kent), U.S. Pat. No. 5,039,660 (issued to Leonard), and U.S. Pat. No. 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

Alternatively, delayed absorption of a parenterally administered drug form can be accomplished by dissolving or suspending the drug in an oil vehicle.

For intramuscular preparations, a sterile formulation of compounds, optionally in conjunction with an antimicrobial, or suitable soluble salt forms thereof, for example hydrochloride salts, can be dissolved and administered in a pharmaceutical diluent such as Water-for-Injection (WFI), physiological saline or about 5% glucose or about 3% glycerol. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, parental, or transmucosal formulation of compounds, preferably a composition, pharmaceutical composition or formulation disclosed herein in conjunction with an antimicrobial and/or glycerol may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions, preferably a composition, pharmaceutical composition or formulation disclosed herein in conjunction with an antibiotic or anti-fungal agent, and glycerol, can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethyl sulfoxide (DMSO) to facilitate surface penetration of the active ingredient.

For application to the eyes or ears, the pharmaceutical composition can be presented in liquid or semi-liquid form formulated in hydrophobic or hydrophilic bases as ointments, creams, lotions, paints or powders.

For rectal and vaginal administration, the pharmaceutical compositions, pharmaceutical composition or formulation disclosed herein in conjunction with glycerol and/or an antimicrobial, can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds, preferably a composition, pharmaceutical composition or formulation disclosed herein in conjunction with glycerol and an antimicrobial agent can be a solution of one or more compounds, or salts thereof, in a suitable diluent, in sterile hermetically sealed ampoules or sterile syringes. The concentration of the compounds, preferably a composition, pharmaceutical composition or formulation disclosed herein in conjunction with an antimicrobial in the unit dosage may vary, e.g. from about 1 percent to about 50 percent, depending on the compound used and its solubility and the dose desired by the physician. If the compositions contain dosage units, each dosage unit can contain from about 1 to about 500 mg of the active material. For adult human treatment, the dosage employed can range from about 5 mg to about 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention, preferably in combination with an antimicrobial for the drugs in the art-recognized protocols.

Exemplary procedures for delivering an antibacterial agent are described in U.S. Pat. Nos. 6,468,967; 6,852,689; and U.S. Pat. No. 5,041,567, issued to Rogers and in PCT patent application number EP94/02552 (publication no. WO 95/05384), the disclosures of which are incorporated by reference in their entirety. In one embodiment, one or more compounds of the invention, preferably compounds and formulations disclosed herein in conjunction with glycerol and an antimicrobial, or pharmaceutical compositions thereof are administered orally, rectally or via injection e.g., intravenous, intramuscular, subcutaneous or transmucosally. In another embodiment, one or more compounds of the invention, preferably a composition, pharmaceutical composition or formulation disclosed herein in conjunction with glycerol, an antimicrobial agent, or pharmaceutical compositions thereof are administered orally, rectally or via injection e.g., intravenous, intramuscular, subcutaneous or transmucosal to treat an infection caused by β-lactamase resistant bacteria. In another embodiment, one or more compounds of the invention, preferably a composition, pharmaceutical composition or formulation disclosed herein in conjunction with an antibiotic, or pharmaceutical compositions thereof are administered orally to treat an infection caused by β-lactamase producing bacteria.

For preparing pharmaceutical compositions from the compounds of this invention, pharmaceutical compositions may comprise inert, pharmaceutically acceptable carriers in either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like. Salts include, but are not limited to, pharmaceutically acceptable salts. Examples of pharmaceutically acceptable salts within the scope of the present invention include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and benzathine.

In some embodiments, pharmaceutical compositions comprise pharmaceutically acceptable salts such as hydrochlorides, sulfates and bitartrates. The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins; methylcellulose, sodium carboxymethyl cellulose, and other suspending agents known to the pharmaceutical formulation art.

Preferably the pharmaceutical composition is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

The pharmaceutical compositions of the instant disclosure or the pharmaceutically acceptable salts derived therefrom may be in a liquid or solid dosage form. Such compositions may include any type of dosage forms such as tablets, capsules, powders, liquid formulations, delayed or sustained release, patches, snuffs, nasal sprays, and the like. The formulations may additionally include other ingredients such as dyes, preservatives, buffers, and antioxidants, for example. The physical form and content of the pharmaceutical formulations contemplated are conventional preparations that can be formulated by those skilled in the pharmaceutical formulation field and are based on well-established principles and compositions described in, for example, Remington: The Science and Practice of Pharmacy, 19th Edition, 1995; *British Pharmacopoeia* 2000, each of which is incorporated herein by reference. The compositions of the present invention may also include other active agents useful in the treatment of cardiovascular conditions. Solid forms can be prepared according to any means suitable in the art. For example, capsules are prepared by mixing the analog composition with a suitable diluent and filling the proper amount of the mixture in capsules. Tablets are prepared by direct compression, by wet granulation, or by dry granulation. Their formulations usually incorporate diluents, binders, lubricants and disintegrators as well as the compound. Diluents, but are not limited to, include various types of starch, cellulose, crystalline cellulose, microcrystalline cellulose, lactose, fructose, sucrose, mannitol or other sugar alcohols, kaolin, calcium phosphate or sulfate, inorganic salts such as sodium chloride and powdered sugar. Powdered cellulose derivatives are also useful. Non-limiting examples of tablet binders include, but are not limited to, starches, gelatin, and sugars such as lactose, fructose, glucose, and the like. Natural and synthetic gums are also convenient, including, but not limited to, acacia, alginates, methylcellulose, polyvinylpyrrolidone, and the like. Polyethylene glycol, ethylcellulose and waxes can also serve as binders.

A lubricant can be used in a tablet formulation to prevent the tablet and punches from sticking in the die. The lubricants include but are not limited to, such slippery solids as talc, magnesium and calcium stearate, stearic acid, and hydrogenated vegetable oils.

Tablets can be coated with sugar as a flavor and sealant or with film-forming protective agents to modify the dissolution properties of the tablet. The compounds may also be formulated as chewable tablets by using large amounts of pleasant-tasting substances such as mannitol in the formulation, as is now well-established in the art.

Also contemplated are liquid formulations and solid-form preparations, which are intended to be converted, shortly before use, to liquid form preparations. Such liquid forms include, but are not limited to, solutions, suspensions, syrups, slurries, and emulsions.

Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder form for constitution with a suitable vehicle, such as sterile water, saline solution, or alcohol, before use. In some embodiments, the oral transmucosal solid dosage further comprises a permeation enhancer. In some embodiments, the permeation enhancer is chosen from: a bile salt, sodium dodecyl sulfate, dimethyl sulfoxide, sodium lauryl sulfate, a derivative of a saturated or an unsaturated fatty acid, a surfactant, a bile salt analog, and a derivative of bile salt. In some embodiments, the oral transmucosal dosage form is chosen from: chewing gum, a patch, a lozenge, a lozenge-on-α-handle, a tablet, a troche, a pastille, a sachet, a sublingual tablet, and a rapidly disintegrating tablet. In some embodiments, the oral transmucosal solid dosage form wherein the composition further comprises at least one flavoring agent, artificial coloring, sweetener, lubricating agent, disintegration agent, lubricating agent, diluent, base, or buffering agent. In some embodiments, the oral transmucosal solid dosage form further comprises a sustained release agent. The invention is directed to a solid dosage form wherein the concentration of analog is from about 0.001% to about 90% of the dry matter weight of the composition.

Solid dosage forms such as lozenges and tablets may also be used for oral delivery of pharmaceuticals. For example, nitroglycerin sublingual tablets have been on the market for many years. The sublingual tablets are designed to deliver small amounts of potent nitroglycerin, which is almost immediately dissolved and absorbed. On the other hand, most lozenges or tablets are typically designed to dissolve in the mouth over a period of at least several minutes, which allows extended dissolution of the lozenge and absorption of the drug. Administration of lozenges or sublingual tablets generally utilize an "open" delivery system, in which the drug delivery conditions are influenced by the conditions of the surrounding environment, such as rate of saliva secretion, pH of the saliva, or other conditions beyond the control of the formulation. A lozenge-on-α-handle (similar to a lollipop) is another dosage form suitable for transmucosal drug delivery. In addition to being non-invasive and providing a particularly easy method of delivery, the lozenge-on-α-handle (or lozenge with an integrated oral transmucosal applicator) dosage form allows a patient or caregiver to move the dosage form in and out of the mouth to titrate the dose. This practice is called dose-to-effect, in which a patient or caregiver controls the administration of the dose until the expected therapeutic effect is achieved. This is particularly important for certain signs and/or symptoms, such as pain, nausea, motion sickness, and premedication prior to anesthesia because each patient needs a different amount of medication to treat these signs and/or symptoms. For these types of treatments, the patient is the only one who knows how much medication is enough. Once the appropriate amount of drug is delivered, the patient or caregiver can remove the lozenge-on-α-handle, thus, stopping the delivery of the drug. This feature is especially important for particularly potent drugs, which may present a significant advantage of terminating drug administration once the desired effect is achieved.

The compositions of the invention can be administered in a sustained release composition, such as those described in, for example, U.S. Pat. Nos. 5,672,659 and 5,595,760, and herein incorporated by reference in their entirety. The use of immediate or sustained release compositions depends on the type of condition being treated.

The pharmaceutical compositions of the instant invention or the pharmaceutically acceptable salts derived therefrom may be in a dosage amount in an effective amount to induce reduction or disruption of biofilms of bacterial, fungal, protozoan cells or viral particles. The pharmaceutical compositions of the instant invention or the pharmaceutically acceptable salts derived therefrom may be in a dosage amount to effect reduction or cessation of growth of a biofilm. The pharmaceutical compositions of the instant invention or the pharmaceutically acceptable salts derived therefrom may be in a dosage amount for an effective amount to reduce or eliminate the signs and/or symptoms of a biofilm-producing microorganism infection.

The dose of the composition or pharmaceutical compositions may vary. The dose of the composition may be once per day. In some embodiments, multiple doses may be administered to the subject daily. In some embodiments, the total dosage is administered in at least two application periods. In some embodiments, the period can be an hour, a day, multiple days, a month, a year, for multiple years, or as needed. In an additional embodiment of the invention, the total dosage is administered in two or more separate application periods or in separate doses. In some embodiments, the methods of administering the pharmaceutical compositions of the disclosure comprise application or administration period of once an hour, once every two hours, once every 6 hours, once every 12 hours, or once a day. In some embodiments, the methods of administering the pharmaceutical compositions of the disclosure comprise an application or administration period of twice an hour or more frequently depending upon the severity of the infection or contamination or to prevent toxic side effects from the destruction of the pathogen. or in the expected time needed to get rid of the infection.

In some embodiments, subjects can be administered the composition in which the composition is provided in a daily dose range of about 0.0001 mg/kg to about 5000 mg/kg for the time needed to eradicate the infecting biofilm microbe and also considering the weight of the subject. The dose administered to the subject can also be measured in terms of total amount of, amino acid and/or amino acid derivative, and/or glycerol. or only glycerol, each day. In some embodiments, a subject is administered from about 0.001 to about 4000 milligrams of glycerol or of amino acid and/or amino acid derivative, with or without glycerol, per day. In some embodiments, a subject is administered up to about 3000 milligrams of glycerol or of amino acid and/or amino acid derivative, with or without glycerol, per day. In some embodiments, a subject is administered up to about 1800 milligrams of glycerol or of amino acid and/or amino acid derivative, with or without glycerol, per day. In some embodiments, a subject is administered up to about 1600 milligrams of glycerol or of amino acid and/or an amino acid derivative, with or without glycerol per day. In some embodiments, a subject is administered up to about 1400 milligrams of glycerol or of amino acid and/or an amino acid derivative, with or without glycerol, per day. In some embodiments, a subject is administered up to about 1200 milligrams of glycerol or of amino acid and/or an amino acid derivative with or without glycerol, per day. In some embodiments, a subject is administered up to about 1000 milligrams of glycerol or of amino acid and/or amino acid derivative, with or without glycerol, per day. In some embodiments, a subject is administered up to about 800 milligrams of glycerol or of amino acid and/or amino acid derivative, with or without glycerol, per day. In some embodiments, a subject is administered from about 0.001 milligrams to about 700 milligrams of glycerol or of amino acid and/or amino acid derivative, with or without glycerol, per dose. In some embodiments, a subject is administered up to about 700 milligrams of glycerol or of amino acid and/or amino acid derivative, with or without glycerol, per dose. In some embodiments, a subject is administered up to about 600 milligrams of glycerol or of amino acid and/or amino acid derivative, with or without glycerol, per dose. In some embodiments, a subject is administered up to about 500 milligrams of glycerol or of amino acid or amino acid derivative, with or without glycerol, per dose. In some embodiments, a subject is administered up to about 400 milligrams of glycerol or of amino acid and/or amino acid derivative, with or without glycerol, per dose. In some embodiments, a subject is administered up to about 300 milligrams of glycerol or of amino acid and/or amino acid derivative, with or without glycerol, per dose. In some embodiments, a subject is administered up to about 200 milligrams of glycerol or of amino acid and/or amino acid derivative, with or without glycerol, per dose. In some embodiments, a subject is administered up to about 100 milligrams of glycerol or of amino acid and/or amino acid derivative, with or without glycerol, per dose. In some embodiments, a subject is administered up to about 50 milligrams of amino acid and/or amino acid derivative, with or without glycerol, per dose.

In some embodiments, subjects can be administered the composition comprising glycerol and/or an amino acid and/or an amino acid derivative or a pharmaceutically acceptable salt thereof, with or without glycerol, in a daily dose range of about 0.0001 mg/kg to about 5000 mg/kg of the weight of the subject. In some embodiments, the composition comprising glycerol or an amino acid and/or an amino acid derivative or a pharmaceutically acceptable salt thereof, with or without glycerol, is administered in a daily dosage of up to about 450 mg/kg of the weight of the subject. In some embodiments, the composition comprising glycerol or an amino acid and/or an amino acid derivative composition or a pharmaceutically acceptable salt thereof, with or without glycerol, is administered in a daily dosage of up to about 400 mg/kg of the 'weight of the subject. In some embodiments, the composition comprising glycerol or an amino acid or an amino acid derivative or a pharmaceutically acceptable salt thereof, with or without glycerol, is administered in a daily dosage of up to about 350 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 300 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 250 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 200 mg/kg of the weight of the subject. In some embodiments, the composition comprising glycerol or an amino acid or an amino acid derivative composition or a pharmaceutically acceptable salt thereof, with or without glycerol is administered in a daily dosage of up to about 150 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 100 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 50 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 25 mg/kg of the weight of the subject.

In some embodiments, the composition comprising glycerol or an amino acid or an amino acid derivative composition or a pharmaceutically acceptable salt thereof, with or without glycerol, is administered in a daily dosage of up to about 10 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 5 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 1 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 0.001 mg/kg of the weight of the subject. In some embodiments, the composition comprising glycerol or an amino acid or an amino acid derivative composition or a pharmaceutically acceptable salt thereof, with or without glycerol, is administered in a daily dosage of up to about 0.001 mg/kg of the weight of the subject. In some embodiments, the composition comprising glycerol or an amino acid or amino acid derivative composition or a pharmaceutically acceptable salt thereof, with or without glycerol, is administered in a daily dosage of up to about 0.001 mg/kg of the weight of the subject. The dose administered to the subject can also be measured in terms of total amount glycerol and, or, of amino acid and/or amino acid derivative composition administered per day.

In some embodiments, a subject in need thereof is administered from about 1 µg to about 500 µg of analog or a pharmaceutical salt thereof, with or without glycerol, per day. In some embodiments, a subject in need thereof is administered from about 1 µg to about 10 µg of analog or a pharmaceutical salt thereof, with or without glycerol, per day. In some embodiments, a subject in need thereof is administered from about 10 µg to about 20 µg of analog or a pharmaceutical salt thereof, with or without glycerol, per day. In some embodiments, a subject in need thereof is administered from about 10 µg to about 100 µg of analog or a pharmaceutical salt thereof, with or without glycerol, per day. In some embodiments, a subject in need thereof is administered from about 100 µg to about 200 µg of analog or a pharmaceutical salt thereof, with or without glycerol, per day. In some embodiments, a subject in need thereof is administered from about 200 µg to about 300 µg of analog or a pharmaceutical salt thereof, with or without glycerol, per day. In some embodiments, a subject in need thereof is administered from about 300 µg to about 400 µg of analog or a pharmaceutical salt thereof, with or without glycerol per day. In some embodiments, a subject in need thereof is administered from about 400 µg to about 500 µg of analog or a pharmaceutical salt thereof, with or without glycerol, per day. In some embodiments, a subject in need thereof is administered from about 500 µg to about 600 µg of analog or a pharmaceutical salt thereof, with or without glycerol, per day. In some embodiments, a subject in need thereof is administered from about 600 µg to about 700 µg of analog or a pharmaceutical salt thereof, with or without glycerol, per day. In some embodiments, a subject in need thereof is administered from about 800 µg to about 900 µg of analog or a pharmaceutical salt thereof, with or without glycerol, per day. In some embodiments, a subject in need thereof is administered from about 900 µg to about 1 µg of analog or a pharmaceutical salt thereof, with or without glycerol, per day. In some embodiments, a subject in need thereof is administered from about 1 µg to about 100 kg of analog or a pharmaceutical salt thereof, with or without glycerol, per day. In some embodiments, a subject in need thereof is administered from about 100 kg to about 200 kg of analog or a pharmaceutical salt thereof, with or without glycerol, per day. In some embodiments, a subject in need thereof is administered from about 200 kg to about 300 kg of analog or a pharmaceutical salt thereof, with or without glycerol per day. In some embodiments, a subject in need thereof is administered from about 300 kg to about 400 kg of analog or a pharmaceutical salt thereof, with or without glycerol, per day. In some embodiments, a subject in need thereof is administered from about 400 kg to about 500 kg of analog or a pharmaceutical salt thereof, with or without glycerol, per day. In some embodiments, a subject in need thereof is administered from about 500 kg to about 600 kg. of analog or a pharmaceutical salt thereof, with or without glycerol, per day. In some embodiments, a subject in need thereof is administered from about 600 kg to about 700 kg of analog or a pharmaceutical salt thereof, with or without glycerol, per day. In some embodiments, a subject in need thereof is administered from about 800 kg to about 900 kg of analog or a pharmaceutical salt thereof, with or without glycerol, per day. In some embodiments, a subject in need thereof is administered from about 900 kg to about 1 mg of analog or a pharmaceutical salt thereof with or without glycerol per day.

In some embodiments, a subject in need thereof is administered from about 0.0001 to about 3000 milligrams of amino acid or amino acid derivative composition or a pharmaceutical salt thereof, with or without glycerol per day. In some embodiments, a subject is administered up to about 2000 milligrams of amino acid or amino acid derivative composition or a pharmaceutical salt thereof, with or without glycerol per day. In some embodiments, a subject is administered up to about 1800 milligrams of amino acid or amino acid derivative composition or a pharmaceutical salt thereof, with or without glycerol, per day. In some embodiments, a subject is administered up to about 1600 milligrams of amino acid or amino acid derivative composition or a pharmaceutical salt thereof, with or without glycerol per day. In some embodiments, a subject is administered up to about 1400 milligrams of amino acid or amino acid derivative composition or a pharmaceutical salt thereof, with or without glycerol per day. In some embodiments, a subject is administered up to about 1200 milligrams of amino acid or amino acid derivative composition or a pharmaceutical salt thereof, with or without glycerol per day. In some embodiments, a subject is administered up to about 1000 milligrams of amino acid or amino acid derivative composition or a pharmaceutical salt thereof, with or without glycerol per day. In some embodiments, a subject is administered up to about 800 milligrams of amino acid or amino acid derivative composition or a pharmaceutical salt thereof, with or without glycerol per day. In some embodiments, a subject is administered from about 0.0001 milligrams to about 700 milligrams of amino acid or amino acid derivative composition or a pharmaceutical salt thereof, with or without glycerol, per dose. In some embodiments, a subject is administered up to about 700 milligrams of amino acid or amino acid derivative composition or a pharmaceutical salt thereof, with or without glycerol per dose. In some embodiments, a subject is administered up to about 600 milligrams of amino acid or amino acid derivative composition or a pharmaceutical salt thereof, with or without glycerol per dose. In some embodiments, a subject is administered up to about 500 milligrams of amino acid or amino acid derivative composition or a pharmaceutical salt thereof, with or without glycerol per dose. In some embodiments, a subject is administered up to about 400 milligrams of amino acid or amino acid derivative composition or a pharmaceutical salt thereof, with or without glycerol per dose. In some embodiments, a subject is administered up to about 300 milligrams of amino acid or amino acid derivative composition or a pharmaceutical salt thereof, with or without glycerol per dose. In some embodiments, a subject is administered up to about 200 milligrams of amino acid or amino acid derivative composition or a pharmaceutical salt thereof, with or without glycerol per dose. In some embodiments, a subject is administered up to about 100 milligrams of amino acid or amino acid derivative composition or a pharmaceutical salt thereof, with or without glycerol per dose. In some embodiments, a subject is administered up to about 50 milligrams of amino acid or amino acid derivative composition or a pharmaceutical salt thereof with or without glycerol per dose. In some embodiments a subject is administered up to about 25 milligrams of amino acid or amino acid derivative composition or a pharmaceutical salt thereof, with or without glycerol per dose. In some embodiments, a subject is administered up to about 15 milligrams of amino acid or amino acid derivative composition or a pharmaceutical salt thereof, with or without, glycerol per dose.

In some embodiments, a subject is administered up to about 10 milligrams/Kg of the weight of the subject of amino acid or amino acid derivative composition or a pharmaceutical salt thereof, with glycerol per dose. In some embodiments, a subject is administered up to about 5 milligrams of amino acid and/or amino acid derivative composition or a pharmaceutical salt thereof, with glycerol per dose. In some embodiments, a subject is administered up to about 1 milligram of amino acid and/or amino acid derivative composition or a pharmaceutical salt thereof, with glycerol per dose. In some embodiments, a subject is administered up to about 0.001 milligrams of amino acid and/or amino acid derivative composition or a pharmaceutical salt thereof, with glycerol per dose. In some embodiments, a subject is administered up to about 0.001 milligrams of amino acid and/or amino acid derivative composition or a pharmaceutical salt thereof, with glycerol per dose.

The dose administered to the subject can also be measured in terms of total amount of glycerol or amino acid and/or amino acid derivative composition or a pharmaceutical salt thereof, with or without glycerol, administered per ounce of liquid prepared. In some embodiments, the glycerol or amino acid and/or amino acid derivative composition or a pharmaceutical salt thereof, with or without glycerol, is at a concentration of from about 0.000001 grams per ounce of composition or a pharmaceutical salt thereof at a concentration of about 2.25 grams per ounce of solution. In some embodiments, the glycerol or amino acid and/or amino acid derivative composition or a pharmaceutical salt thereof, with or without glycerol, is at a concentration of about 2.0 grams per ounce of solution. In some embodiments, the glycerol or amino acid and/or amino acid derivative composition or a pharmaceutical salt thereof, with or without glycerol, is at a concentration of about 1.9 grams per ounce of solution. In some embodiments, the glycerol or amino acid and/or amino acid derivative composition or a pharmaceutical salt thereof, with or without glycerol, is at a concentration of about 1.8 grams per ounce of solution. In some embodiments, the glycerol or amino acid and/or amino acid derivative composition or a pharmaceutical salt thereof, with or without glycerol, is at a concentration of about 1.7 grams per ounce of solution. In some embodiments, the glycerol or amino acid and/or amino acid derivative composition or a pharmaceutical salt thereof, with or without glycerol, is at a concentration of about 1.6 grams per ounce of solution. In some embodiments, the glycerol or amino acid or amino acid derivative composition or a pharmaceutical salt thereof is at a concentration of about 1.5 grams per ounce of solution. In some embodiments, the glycerol or amino acid or amino acid derivative composition or a pharmaceutically salt thereof is at a concentration of about 1.4 grams per ounce of solution. In some embodiments, the glycerol or amino acid or amino acid derivative composition or a pharmaceutically salt thereof is at a concentration of about 1.3 grams per ounce of solution. In some embodiments, the glycerol or amino acid or amino acid derivative composition or a pharmaceutical salt thereof is at a concentration of about 1.2 grams per ounce of solution. In some embodiments, the glycerol or amino acid or amino acid derivative composition or a pharmaceutical salt thereof is at a concentration of about 1.1 grams per ounce of solution. In some embodiments, the glycerol or amino acid or amino acid derivative composition or a pharmaceutical salt thereof is at a concentration of about 1.0 grams per ounce of solution.

In some embodiments, the glycerol or amino acid and/or amino acid derivative composition or a pharmaceutical salt thereof is at a concentration of about 0.9 grams per ounce of solution. In some embodiments, the glycerol or amino acid and/or amino acid derivative composition or a pharmaceutical salt thereof is at a concentration of about 0.8 grams per ounce of solution. In some embodiments, the glycerol or amino acid and/or amino acid derivative composition or a pharmaceutical salt thereof is at a concentration of about 0.7 grams per ounce of solution. In some embodiments, the glycerol or amino acid and/or amino acid derivative composition or a pharmaceutical salt thereof is at a concentration of about 0.6 grams per ounce of solution. In some embodiments, the glycerol or amino acid and/or amino acid derivative composition or a pharmaceutical salt thereof is at a concentration of about 0.5 grams per ounce of solution. In some embodiments, the glycerol or amino acid and/or amino acid derivative composition or a pharmaceutical salt thereof is at a concentration of about 0.4 grams per ounce of solution. In some embodiments, the glycerol or amino acid and/or amino acid derivative composition or a pharmaceutical salt thereof is at a concentration of about 0.3 grams per ounce of solution. In some embodiments, the glycerol or amino acid and/or amino acid derivative composition or a pharmaceutical salt thereof is at a concentration of about 0.2 grams per ounce of solution. In some embodiments, the amino glycerol or acid and/or amino acid derivative composition or a pharmaceutical salt thereof is at a concentration of about 0.001 grams per ounce of solution. In some embodiments, the glycerol or amino acid and/or amino acid derivative composition or a pharmaceutical salt thereof is at a concentration of about 0.001 grams per ounce of solution. In some embodiments, the glycerol or amino acid and/or amino acid derivative composition or a pharmaceutical salt thereof is at a concentration of about 0.001 grams per ounce of solution prepared. In some embodiments, the glycerol or amino acid and/or amino acid derivative composition or a pharmaceutical salt thereof is at a concentration of about 0.0001 grams per ounce of solution prepared. In some embodiments, the glycerol or amino acid and/or amino acid derivative composition or a pharmaceutical salt thereof is at a concentration of about 0.00001 grams per ounce of solution prepared. In some embodiments, the glycerol or amino acid and/or amino acid derivative composition or a pharmaceutical salt thereof is at a concentration of about 0.000001 grams per ounce of solution prepared.

For systemic infections, an appropriate antimicrobial may be administered at an appropriate concentration and period of time plus an appropriate concentration of glycerol by intravenous or transmucosal administration.

For infections not in contact with plasma, an appropriate amount of antimicrobial antibiofilm amino acids and/or amino acids with or without glycerol would have to be applied to the infected area for a sufficient time depending on the clinical response.

In some embodiments, viral bacteriophages make it possible to reduce or eliminate colonization and/or infection of humans and animals by pathogenic bacteria, including antibiotic resistant bacteria. Compared to antibiotics, in some embodiments, phages go deeper into the infected area. Antibiotics, on the other hand and in some embodiments, have concentration properties that quickly decrease as they go below the surface of the infection. The replication of phages is concentrated on the infected area where they are needed the most, while antibiotics are metabolized and removed from the body. In addition, secondary resistance does not happen among phages, but happens quite often among antibiotics. Secondary resistance is acquired and occurs when there are not enough blood drug levels. Phages, in some embodiments, provide a good choice for the treatment of drug-resistant bacteria.

In some embodiments, the viral bacteriophages are chosen from phages belonging to a family chosen from ampullaviridae, bicaudaviridae, clavaviridae, corticoviridae, cystoviridae, fuselloviridae, globulos viridae, guttaviridae, inoviridae, leviviridae, microviridae, plasmaviridae, tectiviridae.

In some embodiments, the viral bacteriophages are used as a single phage or in combination (including any other phage belonging to a family chosen from ampullaviridae, bicaudaviridae, clavaviridae, corticoviridae, cystoviridae, fuselloviridae, globulos viridae, guttaviridae, inoviridae, leviviridae, microviridae, plasmaviridae, tectiviridae, and/or others.

In some embodiments, the antihistamines are chosen from azelastine, hydroxyzine, desloratadine, emadastine, levocabastine, azelastine, carbinoxamine, and levocetirizine. In some embodiments, the antihistamines are chosen from fexofenadine, diphenhydramine, dimetane, loratadine, clemastine, chlorpheniramine, and certirizine. In some embodiments, the antihistamines are chosen from brompheniramine, chlorpheniramine, dimenhydrinate, and doxylamine.

In some embodiments, the nasal decongestants are chosen from oxymetazoline, phenylephrine, and pseudoephedrine.

In some embodiments, the active ingredients are chosen from spermicidal agents, prostaglandins, and hormones.

In some embodiments, the pharmaceutical composition is contained within or embedded within a mucoadhesive polymer. Such polymers are chosen from protein-based polymers, polysaccharides, polyesters, polyanhydrides, polyamides, phosphorus-based polymers, acrylic polymers, vinylpyrrolidone polymers, celluloses, and silicones.

In some embodiments, the mucoadhesive polymers have a mass average molecular weight above about 75,000 Da to about 20,000,000 Da. In some embodiments, the average molecular weight ranges from about 100,000 to about 20,000,000 Da or from about 200,000 to about 1,000,000 Da or from about 400,000 to about 700,000 Da.

In some embodiments, the mucoadhesive polymers in general, include hydrophilic polymers and hydrogels. In the large classes of hydrophilic polymers, those containing carboxylic group exhibit mucoadhesive properties; these include polyvinyl pyrrolidone (PVP), methyl cellulose (MC), sodium carboxy-methylcellulose (SCMC) hydroxypropyl cellulose (HPC) and other cellulose derivative. Hyrogels are the class of polymeric biomaterials that exhibit the basic characteristics of swelling by absorbing water, and then they interact with the mucus that covers epithelium by means of adhesion. Polymers with anionic groups include: carbopol, polyacrylates and their cross-linked modifications, polymers with cationic groups include chitosan and its derivatives and aminoethyl methacrylate or acrylate polymers.

One or more of the following basic properties of a polymer indicate a good mucoadhesive profile: high molecular weight, chain flexibility, high viscosity, optimal cross-linked density of polymer, charge and degree of ionization of polymer (anion>cation>unionized), medium pH, hydration of the polymer, high applied strength and duration of its application and high initial contact time. In addition to the above factors, some physiological factors, like mucin turnover and disease status also affect the mucoadhesion. The mucin turnover is expected to limit the residence time of the mucoadhesive agents on the mucus layer. This could detach mucoadhesives from the surface no matter how high the mucoadhesive strength may be.

In some embodiments, the mucoadhesive system should possess an acceptable active ingredient loading capacity, good mucoadhesion, no irritancy, good feel in the place of administration, sustained drug delivery and an erodible formulation has the added advantage of not requiring retrieval after delivery of the dose. Therefore, hydrophilic polymers with good ability to stick to mucosal membranes are a good choice. They normally possess charged groups or nonionic functional groups capable of forming hydrogen bonds with mucosal surfaces. To accomplish these properties, structural characteristics such as strong hydrogen bonding groups (e.g. carboxyl, hydroxyl, amino- and sulfate groups), strong anionic or cationic charges, high molecular weight, chain flexibility, and surface energy properties favoring spreading onto mucus are sought.

In some embodiments, anionic polymers have demonstrated mucoadhesive properties related to the ability of carboxylic groups to form hydrogen bonds with oligosaccharide chains of mucins. In some embodiments, weakly anionic carboxyl-containing polymers such as poly(acrylic acid), poly-(methacrylic acid), sodium alginate, carboxymethylcellulose and poly(maleic acid)-co-(vinyl methyl ether) are used. In some embodiments, chitosan and some synthetic polymethacrylates are cationic polymers that have mucoadhesiveness. This property has been related to their ability to interact with negatively charged mucins via electrostatic attraction, and hydrophobic effects may also play a certain role. In some embodiments, chitosan derivatives relevant to pharmaceutical applications include trimethyl chitosan, glycol chitosan, carboxymethylchitosan and half-acetylated chitosan. In some embodiments, solid micro/nanoparticulate systems based on chitosan and derivatives have been the focus of several studies.

In some embodiments, compared to the charged, non-ionic polymers generally show lesser mucoadhesiveness. The specific interactions between mucin and these kinds of polymers are usually very weak. In some embodiments, amphoteric polymers such as gelatin and carboxymethylchitosan, have been explored as mucoadhesive materials for pharmaceutical systems. In some embodiments, their nature of and self-neutralization of cationic and anionic charges within their structure contribute to relatively lesser mucoadhesiveness, similar to non-ionic polymers. In some embodiments, animated derivative of gelatin has shown a considerable gastric mucoadhesion both in vitro and in vivo in rats.

In some embodiments, polyampholyte polymers displayed particular characteristics that have to be taken into consideration with regard to their mucoadhesive and penetration-enhancing properties. In some embodiments, they exist positively charged, neutral and negatively charged, depending on dispersion pH and their specific isoelectric point. In some embodiments, the viscosity in the dispersion is minimal and increases when pH is higher or smaller than the isoelectric point.

In some embodiments, the presence of inorganic salts affects the viscosity of the dispersion. In some embodiments, the mucoadhesive and penetration-enhancing properties of polyampholyte-based formulations are affected by all these pH-induced structural and physicochemical transformations.

In some embodiments, there is another specific class of polymers called thiomers. They are characterized by containing side chains with thiol-bearing functional groups and are obtained by conjugating conventional mucoadhesive polymers with molecules carrying thiol functionality. The presence of this kind of functional group enables the formation of disulfide bridges (covalent bonds) with cysteine-rich sub-domains of mucus glycoproteins either via thiol/disulfide exchange reactions or through simple oxidation of free thiol groups, exhibiting significantly enhanced mucoadhesive properties in comparison with conventional mucoadhesives. In some embodiments, poly(acrylic acid)/cysteine, chitosan/N-acetylcysteine, alginate/cysteine, chitosan/thioglycolic acid, and chitosan/thioethylamidine are typical polymeric thiomers. The development of novel derivatization approaches to thiolate non-ionic polymers may offer a way to improve their poor mucoadhesive performance. In some embodiments, the polymers have acrylate end groups. They are a class of mucoadhesive polymers capable of forming covalent bonds with mucins similar to polymeric thiomers.

In some embodiments, dendrimers have displayed usefulness as mucoadhesives due to their properties and unique structure. In some embodiments, poly(amidoamine) (PAMAM) dendrimers carrying various functional groups (amino, carboxyl and hydroxyl surface groups, COOH) are chosen for mucoadhesiveness. In some embodiments, boronic acid copolymers are chosen for mucoadhesiveness. In some embodiments, copolymers of N-acryloyl-m-aminophenylboronic acid with N,N-dimethylacrylamide (e.g., up to 15 mol-% N-acryloyl-m-aminophenylboronic acid to ensure their solubility in aqueous environment) display interactions with stomach mucin and may facilitate the retention of poly(vinyl alcohol)/borax gels in mucosal lumens, mainly at pH 7.0-9.0, where their complexation with mucins is pronounced.

In some embodiments, polymers containing sugar moieties as pendant groups (synthetic glycopolymers) possess hybrid properties. With this kind of material, it is possible for the easy manipulation in their architecture and physicochemical properties, which can be performed through homo- and copolymerization with monomers of different nature.

For example, glycopolymers have been obtained by free-radical copolymerization of N-(2-hydroxypropyl) methacrylamide with various sugar-containing monomers such as N-methacryloylglycylglycylgalactosamine, N-methacryloylglycylglycylfucosylamine, N-methacryloylglycylglycylglucosamine, and N-methacryloylglycylglycylmannosamine. In some embodiments, fucosylamine with copolymers are chosen, e.g., to adhere selectively to the colon in vitro, and stronger adhesion was observed for copolymers containing larger quantities of sugar moieties. The inventors hypothesized that this adhesion is related to the binding of sugar-moieties of the copolymers to specific receptors present in the colonic epithelium. The adhesion of these glycopolymers to the small intestinal mucosa was less pronounced and less sensitive to fucosamine in the copolymers.

In some embodiments, considering the great number of polymers used for developing such systems, one is derived from polyacrylic acid, such as polycarbophil and carbomers; polymers derived from cellulose, such as hydroxyethylcellulose and carboxymethylcellulose; alginates, chitosan and derivatives, lectins and their derivatives are chosen.

In some embodiments, the protein-based polymers are chosen from collagens, albumins, and gelatins. In some embodiments, the albumin is conjugated to poly-(ethylene glycol).

In some embodiments, the polysaccharides are chosen from alginates, cyclodextrines, chitosans, dextrans, agarose, hyaluronic acid, starch, and cellulose.

In some embodiments, the polyesters are chosen from poly lactic acid (PLA), polyglycolic acid (PGA), poly lactide-co-glycolide (PLGA), polyhydroxybutyrate (PHB), poly(e-caprolactone), polydioxanone.

In some embodiments, the celluloses are chosen from carboxymethyl cellulose (CMC), methyl cellulose (MC), hydroxyethylcellulose (HEC), hydroxypropyl methyl cellulose (HPMC), hydroxylpropyl cellulose (HFC), ethyl hydroxyethyl cellulose (EHEC), and methyl hydroxyethyl cellulose (MHEC).

In some embodiments, the mucoadhesive polymer has one or more strong hydrogen bonding groups chosen from OH and COOH.

In some embodiments, the mucoadhesive polymer is chosen from high molecular weight homo- and copolymers of acrylic acid crosslinked with a polyalkenyl polyether. In some embodiments, the mucoadhesive polymer is chosen from crosslinked acrylic or methacrylic acid-based polymers. For example, in some embodiments, the mucoadhesive polymer is chosen from Carbopol or Carbomer brand polymers. For example, in some embodiments, the mucoadhesive polymer is chosen from Carbopol® 934 Polymer, Carbopol® 940 Polymer, Carbopol® 941 Polymer, Carbopol® 980 Polymer, Carbopol® 981 Polymer, Carbopol® 1342 Polymer (Acrylates/C10-30 Alkyl Acrylate Crosspolymer), Carbopol® 1382 Polymer (Acrylates/C10-30 Alkyl Acrylate Crosspolymer), Carbopol® 2984 Polymer, Carbopol® 5984 Polymer, Carbopol® SC-200 Polymer (Acrylates/C10-30 Alkyl Acrylate Crosspolymer, and Carbopol® Silk 100 Polymer. In some embodiments, the mucoadhesive polymer is Carbopol® 940 Polymer.

In some embodiments, the mucoadhesive polymer is chosen from hydroxypropyl propyl cellulose (HPC) or hydroxypropyl methyl cellulose (HPMC).

In some embodiments, the mucoadhesive polymer has an anionic charge.

Another strategy to adjust mucoadhesive properties of the system, is to optimize their mechanical characteristics and modulate their swelling behavior or to improve their biocompatibility to use the polymer blends. New mucoadhesive blends may be obtained by mixture of pharmaceutical polymers in solid state or in solution. When two of these mucoadhesive materials are blended, their mucoadhesive properties are dependent on the strength of specific interactions occurring between both components upon hydration. When there is not the formation of insoluble polycomplexes, the specific interactions between the polymers are not very strong and the mucoadhesiveness of a system will often be intermediate between the adhesiveness of each individual component. Interpolymer complexes such as poly (carboxylic acids) and non-ionic polymers in solutions via hydrogen bonding results in formation of novel polymeric materials-interpolymer complexes. These materials can potentially be used for design of novel mucoadhesive dosage forms.

Preparation of Amino Acid and/or Glycerol Compounds of the Invention

Sterile, non-bonded, amino acids, amino acid derivatives, and glycerol may be purchased from suppliers in a commercial grade with levels of high purity and then added to a volume of liquid. It has been found that it is important to closely control the process steps in combining the various ingredients to form such a complete diet, or various portions thereof, in order to prevent degradation of individual ingredients and/or interactions between ingredients. Thus, after appropriately selecting the levels of amino acids and/or amino acid derivatives and/or glycerol to be employed in the formulation in order to avoid inherently incompatible flavors, as previously indicated, highly pure forms of the amino acids, amino acid derivatives, and glycerol, are used. Recrystallizations of individual amino acids, amino acid derivatives, and glycerol are carried out, if necessary, in order to be sure of the absence of undesirable trace contaminants. After proper selection is made and adequate purity is obtained, close control of the process conditions is used to assure ultimate palatability.

In general, certain amino acids and amino acid derivatives are not very water soluble, and such relatively insoluble members are used in the form of the hydrochloride salts and/or esters thereof, which may degrade into their elemental forms. In order to promote the dissolution of the various amino acids in water, the water is usually maintained at a temperature of about 90 C. to 100 C. However, in some embodiments, it has been found that one of the amino acids or an amino acid derivative of the formulation is too susceptible to thermal degradation to permit its inclusion into the aqueous solution at such temperatures without seriously harming the efficacy of the liquid dosage form. One such ingredient is the non-essential amino acid glutamine. Particular carbohydrates from the group of monosaccharides, disaccharides, starches and dextrins, which may be suitably employed have various degrees of water solubility, and good solubility is desirable in formulating the dosage form.

The non-essential amino acid, aspartic acid, has solubility difficulty in water even at temperatures in the range of about 90 C. to 100 C. However, it has been found that aspartic acid can be fairly readily dissolved in alkaline water having a pH between about 8 and 14. Thus, the dissolution is facilitated by separately dissolving the aspartic acid in alkaline water having a pH of about 8 or above and then adding this pre-solution to the main solution. In some dosage forms, the pH of a liquid dosage form is from about a pH of 8 to about a pH of 10, but the aspartic acid or salt thereof is stored in alkaline conditions before addition to the solution.

Interactions fairly readily occur at elevated temperature between aldehyde or ketone groups present in the carbohydrate component, such as in glucose. In some embodiments, the solution comprises glucose, (or potential aldehyde groups of a glucose-containing polymer subject to hydrolysis) and the amino acids, particularly lysine. Such interaction results in the formation of condensation products which are brown in color and which have a flavor resembling caramel. In some embodiments methods of making the liquid dosage forms comprise steps taken to minimize the extent of the time-temperature integral over which amino acids and amino acid derivatives, glycerol and carbohydrates are present in the solution in order to thereby minimize the extent of caramelization that may occur. This result is achieved most expeditiously by adding the carbohydrate rapidly while agitating the solution to enhance its dissolution. In this respect, the addition of the carbohydrate components, such as glucose, should be sufficiently rapid to drop the temperature to about 40 C. within ten minutes time from the initial addition. It should also be understood that not only does rapid dissolution avoid unpalatability resulting from interaction between amino acids and the aldehyde or ketone groups of the carbohydrate, but it reduces the time at which the methionine is exposed to the relatively high temperatures. Generally, not all of the carbohydrate is added at this time, although it all could be added at this time if one would so desire, and the remainder is dissolved subsequently in the process.

Although it is considered that the stated formulation has advantages from a cost standpoint and from case of formulation, various minerals may be provided as part of the dosage form in a percentage or trace levels within the solution. Magnesium, for instance, might be provided in the form of acetate, citrate or chloride in some embodiments. Similarly, potassium might be provided in the form of bicarbonate or sorbate. Likewise, iron might be provided in the form of chloride, gluconate, acetate or citrate. Calcium may be supplied as acetate, citrate or bicarbonate. Iodine may be provided as the iodide of sodium, magnesium or manganese. Manganese might be provided as manganous chloride, and zinc could be provided as the acetate. Still other suitable forms may also be used.

In some embodiments, the addition to the foregoing minerals, if it is intended to employ the oral or topical dosage form for extended periods of time, metabolizable and nontoxic salts of cobalt and molybdenum are also included. Examples of such suitable salts include sodium, potassium, and ammonium molybdate and cobaltous acetate-4H O.

The order of addition of these minerals is important in order to avoid potential interactions which might result in precipitates that will adversely affect the solution. Magnesium oxide, which is utilized as the source of magnesium, is readily incorporated into the main solution of essential and non-essential amino acids plus carbohydrate by first being dissolved in an aqueous solution of potassium hydroxide and glucono-delta-lactone to form a pre-solution. The pre-solution in which the magnesium oxide is completely dissolved is slowly added to the main solution.

In some embodiments, hydrated sodium glycerophosphate is added to the solution, as is hydrated ferrous ammonium sulfate. The sodium chloride may also be conveniently added at this time. Following the dissolution of the glycerophosphate and the ferrous compounds, the remainder of the carbohydrate is dissolved in the solution, using constant stirring. The temperature of the solution may be raised slightly in order to expedite the solution of the carbohydrate but the temperature should not exceed 35 C.

At this point which is approaching the end of the dissolution process, water-soluble vitamins can be added, one after another, ensuring that each is dissolved before the following one is added. Adding the vitamins earlier and/or while the temperature is higher, is avoided because of the thermal susceptibility of these vitamins, particularly thiamine, for example.

The hydrated calcium chloride is added after the dissolution of the remainder of the carbohydrate. It is extremely important that all of the glycerophosphate compound be completely in solution before the addition of the calcium chloride, and moreover, the addition of the calcium should not immediately follow addition of the glycerophosphate compound because of the potential formation of a refractory precipitate of calcium glycerophosphate. It has been found that such formation of a refractory precipitate is completely avoided if the remainder of the carbohydrate, and preferably also the vitamins, are dissolved in the solution between the initial addition of the glycerophosphate compound and the subsequent dissolution of the soluble calcium compound. It is believed that the glycerophosphate is complexed in some manner by the other ions after a sufficient residence in solution.

In some embodiments, the compositions or pharmaceutical compositions comprise trace amounts of minerals, which can be dissolved in water, and these solutions combined to form one pre-solution. In some methods of making the compositions in solution format, this pre-solution includes the manganous salt, the cupric salt, the zinc salt and the iodide salt, plus the molybdenum and the cobalt salts if such are employed. At this point in the process, the temperature of the main solution is maintained at about 30 C. or below while the pre-solution of the trace minerals is slowly added. Particularly important is the handling of the manganous salt. It has been found that the manganous salt should not be added to the solution prior to the complete dissolution of the water-soluble iron compound, for it appears that a stable solution is not obtained if these two salts are added in the reverse order to a solution containing the amino acids and carbohydrates. It is believed that addition in the reverse order may cause oxidation of the manganous ion to manganese dioxide accompanied by the formation of undesirable precipitates. It is thought that the other ingredients in the solution may well form stable complexes with the ferrous iron if it is added sufficiently prior to the addition of the manganous iron, and accordingly the ferrous ion should preferably be dissolved in the solution prior to the second addition of carbohydrate.

Another consideration in making a composition of this type is that the growth of microorganisms such as bacteria should be prevented. In some embodiments, the solution or liquid dosage form comprises an antibiotic. In some embodiments, the hypertonicity of the solution is controlled such that from the time the temperature is lowered by the first dissolution of the carbohydrate, the amount of water present in the solution, relative to the amount of carbohydrate and solutes, is regulated so that the solution is hypertonic. For purposes of some embodiments, hypertonic solution is defined as having an osmotic pressure higher than that within microorganisms so that undesirable microorganisms, for example, *Escherichia coli*, cannot grow in the solution. The amounts of water added subsequently throughout the process are similarly balanced with the amounts of additional solute so that the hypertonicity of the solution is maintained, at least up to and through the addition of all the water-soluble ingredients.

In some embodiments, the amino acids and the amino acid derivatives of the invention comprise a modification on their side chain or N or C terminus. Modification such as a thiol modification, for instance, can be performed by a reaction of introducing a protected or non-protected thiol group at the R carbon atom of the amino acid derivative is not particularly limited as long as it is a reaction that introduces a protected or non-protected thiol group at the R carbon atom of the amino acid derivative. Introduction may also be carried out after introducing a leaving group at the R carbon atom of the amino acid as an exchange reaction with the leaving group.

For example, this reaction can be carried out by reacting the amino acid derivative with a thiol compound. In terms of introducing a protected thiol group, it is preferred to employ a thiol compound having a protecting group and a hydrogen atom bound to the sulfur atom. Thiol compounds can include benzyl mercaptans or tritylthiols that may possess any number of substituents such as a halogen atom such as fluorine, chlorine, bromine, and iodine, an lower alkyl group having 1-4 carbons such as a methyl group and an ethyl group, an alkoxy group having 1-4 carbons such as a methoxy group and an ethoxy group, and a nitro group at any position on the phenyl ring, alkanethiols such as methanethiol, ethanthiol, and t-butanethiol, acyl thiols that can be easily converted into an acetamidomethyl group, a trityl group, and a disulfide group and the like.

The amount of the thiol compound used may be 1-100 equivalents, preferably 2-20 equivalents, and further preferably 3-10 equivalents to 1 equivalent of the amino acid derivative to be the raw material. Examples of the solvent used can include THF, DCM, DMSO, DMF, and the like, and among these DMF is preferred. The reaction can be carried out in a reaction condition of e.g., at 1-100° C., preferably 10-80° C., and further preferably 15-35° C. for example 30 minutes-24 hours.

The raw material compound of this reaction may be an amino acid or an amino acid derivative that can have a thiol group introduced at the β-position. In other words, the raw material compound may be an amino acid, or may be an amino acid derivative having the amino group, carboxyl group, side chain substituent, and the like of the amino acid protected or substituted by a substituent. In one aspect of the present invention, in terms of efficiently carrying out the reaction, it is preferably an amino acid derivative possessing a leaving group at the β-position, and more preferably an amino acid derivative possessing a halogen atom at the β-position. Moreover, in one aspect of the present invention, in terms of preventing side reactions to increase the yield, it is preferably an amino acid derivative having the amino group and carboxyl group of the amino acid protected.

The reaction of converting the amino group or carboxyl group bound to the α carbon atom of an amino acid derivative into a substituent to be the substrate for a hydrolase selective for D- or L-amino acids is not particularly limited as long as it is a reaction that yields an amino acid derivative having a substituent to be the substrate for a hydrolase selective for D- or L-amino acids bound to the α carbon atom after the reaction. "The amino group or carboxyl group bound to the α carbon atom of an amino acid derivative" in the starting material of the reaction may be a protected or non-protected amino group or carboxyl group. In other words, it may be an unprotected free amino group or carboxyl group, or it may be an amino group or carboxyl group protected by a protecting group. In one aspect of the present invention, when carrying out this reaction after introducing a thiol group at the β-position of the amino acid derivative, if an amino acid derivative having a thiol group introduced at the β-position is used as the raw material and the amino group and carboxyl group are protected for thiolation, the reaction can be carried out using an amino acid derivative having these protected as the raw material.

A group that can be generally employed as the protecting group of the amino group can be employed as the protecting group of the amino group, and e.g., a lipophilic protecting group described below etc. can be employed. For example, in one aspect of the present invention, examples can include a protecting group such as a 9-fluorenylmethoxycarbonyl (Fmoc) group or a t-butyloxycarbonyl (Boc) group, a carbonate-containing group such as an allyloxy carbonate (Alloc) group, an acyl group such as an acetyl (Ac) group, an aryl group, a benzyl group, and the like. In order to introduce a protecting group, e.g., when introducing a Boc group, this can be carried out by e.g., a method of adding a THF solution of Boc2O to the reaction system. The introduction of the protecting group of the amino group can be carried out with the above method as well as well-known methods according to the protecting group. Moreover, the deprotection of the protecting group of the amino group can be carried out by treatment with an acid or a base. For example, when the protecting group is a Boc group, an acid such as trifluoroacetic acid (TFA) can be used. In doing so, this is preferably carried out in the presence of a solvent, examples of which can include DCM, THF, acetonitrile, and the like. The deprotection of the protecting group of the amino group can be carried out with the above method as well as ordinary methods.

A group that can be generally employed as the protecting group of the carboxyl group can be employed as the protecting group of the carboxyl group, for example a lipophilic protecting group described below etc. can be employed. For example, in one aspect of the present invention, examples include protection as an ester by an alkyl group such as a methyl group, an ethyl group, and a tert-butyl group, or an arylalkyl group such as a benzyl group. When the protecting group of the carboxyl group is a methyl group, methyl esterification can be carried out e.g., by a method of adding thionyl chloride and methanol. The introduction of the protecting group of the carboxyl group can be carried out with the above method as well as well-known methods depending on the protecting group. Moreover, the deprotection of the protecting group of the carboxyl group can be carried out by treatment with an acid or a base. For example, when the protecting group is a methyl group, a base such as sodium hydroxide can be used. In doing so, this is preferably carried out in the presence of a solvent, examples of which can include THF, dioxane, acetonitrile, and the like. The deprotection of the protecting group of the carboxyl group can be carried out with the above method as well as ordinary methods.

Methods of Using, Methods of Treating and Preventing Infection with the Amino Acid and/or Glycerol Compositions In another embodiment of the invention, the composition of the invention is used to treat a patient suffering from, or susceptible to, bacterial infection, fungal infection, protozoan infection, or a particular viral infection. In another embodiment of the invention, the composition of the invention is used to treat a patient suffering from, or susceptible to, bacterial infection, fungal infection; protozoan infection, or a known viral infection, characterized as comprising a biofilm. In some embodiments, the compositions or pharmaceutical compositions of the disclosure are used to disrupt a biofilm or biofilms comprising one or a plurality of bacterial cells on the surfaces of a subject or a surface of an inanimate object, such as a laboratory bench, table top, implant (before or after implantation into a subject), or a catheter (before or after fluid communication with a subject is achieved). In some embodiments, the compositions or pharmaceutical compositions of the disclosure are used to disrupt a biofilm or biofilms comprising one or a plurality of fungal cells. In some embodiments, the compositions or pharmaceutical compositions of the disclosure are used to disrupt a biofilm or biofilms comprising one or a plurality of protozoan cells, one or a plurality of bacterial cells and/or fungal cells, or a virus particle. In some embodiments, the disclosure relates to methods of preventing bacterial biofilm formation and/or fungal biofilm formation and/or protozoan biofilm formation or biofilm formation induced by a virus by administration of any of the pharmaceutical compositions disclosed herein, individually or in combination, to a subject in need thereof in a prophylactically effective amount. In some embodiments, the disclosure relates to methods of simultaneously preventing bacterial biofilm formation and fungal biofilm formation by administration of any of the pharmaceutical compositions disclosed herein, individually or in combination, to a subject in need thereof in a prophylactically effective amount. In some embodiments, the disclosure relates to methods of treating a bacterial infection caused by or comprising a bacterial biofilm and/or treating a fungal infection caused by or comprising a fungal biofilm by administration of any of the pharmaceutical compositions disclosed herein, individually or in combination, to a subject in need thereof in a therapeutically effective amount. In some embodiments, the disclosure relates to methods of simultaneously treating a bacterial biofilm infection and a fungal biofilm infection by administration of any of the pharmaceutical compositions disclosed herein in a therapeutically effective amount, individually or in combination (sequentially or simultaneously), to a subject in need thereof.

The disclosure relates to the treatment and/or prevention of fungal infections in a subject caused by fungal cell biofilm formation. In some embodiments, the fungal cells comprise one or a plurality of cells derived from: *Candida albicans*, *Candida guilliermondii*, *Candida parapsilosis*, *Candida glabrata*, *Candida tropicalis* and/or *Candida dubliniensis*.

The disclosure relates to the treatment and/or prevention of bacterial infections in a subject caused by bacterial biofilm formation. In some embodiments, methods of the disclosure relate method of treatment and/or prevention of bacterial cell biofilm formation in a subject by administration of a therapeutically or prophylactically effective amount of one or more of the pharmaceutical compositions of the disclosure. In some embodiments, the bacterial cells comprise one or a plurality of cells derived from: *Staphylococcus aureus* (standard wild type and methicillin-resistant strain USA300), *Escherichia coli*, *Pseudomonas aeruginosa* and/or *Staphylococcus epidermidis*.

In any embodiments of the aforementioned methods, the administration may be accomplished by administration intravenously, topically, irrigation of wounds either as part of a wound dressing or in a sterile solution, intradermally, intramucosally, subcutaneously, sublingually, orally, intravaginally, intramuscularly, intracavernously, intarocularly, intranasally, into a sinus, intrarectally, gastrointestinally, intraductally, intrathecally, subdurally, extradurally, intraventricular, intrapulmonary, into an abscess, intra articular, into a bursa, subpericardially, intrauterine, into the pleural space, swish and swallow treatment of oral candidiasis, transmucosal, or transdermal administration of the prophylactically or therapeutically effective amount of a composition or pharmaceutical composition disclosed herein to a subject in need thereof. In some embodiments, the method comprises administration of an antibiotic prior to, simultaneously with, or subsequent to administration of the prophylactically or therapeutically effective amount of a composition or pharmaceutical composition disclosed herein to a subject in need thereof. In any of the above methods, the method may comprise administration of an antibiotic or anti-fungal agent intravenously, topically, irrigation of wound either as part of wound dressing or in sterile solution, intradermaly, submucosally, subcutaneously, sublingually, orally, intravaginally, intramuscularly, intracavernously, intraocularly, intranasally, into a sinus, intrarectally, gastrointestinally, intraductally, intrathecally, subdurally, extradurally, intraventricular, intrapulmonary, into an abscess, intraarticular, into a bursa, subpericardially, intrauterine, into the pleural space, into the peritoneal cavity, swish and swallow treatment of oral candidiasis, for transmucosal, or for transdermal administration.

If, for instance, the pharmaceutical compositions are administered intracavernously, the pharmaceutical compositions comprise, in some embodiments, a pharmaceutically effective amount of one of the compositions disclosed herein and a pharmaceutically acceptable carrier which may be in solution form and contacted with a wound or in a solution or solid form as part of a wound dressing. The wound dressing may be physically applied in contact to a wound or the skin. In some embodiments, the pharmaceutical compositions are administered as a mouthwash or rinse that is designed not to be ingested but rather swished and spit out.

The pharmaceutical compositions of the disclosure may also include glycerol and/or a retinoid that can be topically administered in any formulation, including a gel or liquid solution or in a spray. A sufficient amount of the topical preparation can be gently rubbed onto the affected area and surrounding skin, for example, in an amount sufficient to cover an affected area plus a margin of healthy skin or tissue surrounding the affected area, for example, a margin of about 0.5 inches. The compositions can be applied to any body surface, including, for example, a skin surface, scalp, face, eyebrows, eyelashes, bearded areas, nail surface, nail bed, nail matrix, and nail fold, as well as to the mouth, vagina, eye, nose, or other mucous membranes.

In some superficial fungal infections of the skin, the composition is applied in a single application four times a day to once a month or, once a week, once bi-weekly, once a month, or from one to four times daily, for a period of time sufficient to alleviate signs and/or symptoms or clear the fungal infection. For example, for a period of time of one week, from 1 to 12 weeks or more, from 1 to 10 weeks, from 1 to 8 weeks, from 2 to 12 weeks, from 2 to 10 weeks, from 2 to 8 weeks, from 2 to 6 weeks, from 2 to 4 weeks, from 4 to 12 weeks, from 4 to 10 weeks, from 4 to 8 weeks, from 4 to 6 weeks. The present compositions can be administered, for example, at a frequency of once per day or twice per day. The presently described compositions can be topically administered once per day for a period of time from 1 week to 8 weeks, from 1 week to 4 weeks, for 1 week, for 2 weeks, for 3 weeks, for 4 weeks, for 5 weeks, for 6 weeks, for 7 weeks, or for 8 weeks.

The presently described compositions can be applied in a therapeutically effective amount, for example, an amount sufficient to cover an affected area plus a margin of healthy skin or tissue surrounding the affected area, for example, a margin of about 0.5 inches. Suitable amounts, for example, per application per affected area or cumulative daily dosage per affected area (for example two applications in a 24 hour period), can include, for example, from about 0.001 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

For example, generally for *Tinea corporis*, or *Tinea cruris*, or *Tinea faciei*, the present composition with/or without glycerol and/or a retinoid can be applied, for example, once or twice daily, for example, morning and evening, for about 2-4 weeks. Generally, for *Tinea pedis* application, the present composition can be applied once daily, for 2 weeks or longer.

For example, the presently described compositions with/or without glycerol and/or a retinoid can be topically applied in an amount sufficient to cover an affected area plus a margin of healthy skin or tissue surrounding the affected area, for example, a margin of about 0.5 inches, at a frequency, for example, of once a day, for a time period, for example of about two weeks.

If desired, other therapeutic agents such as glycerol and retinoids such as trans-retinoic acid can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

In some embodiments, the pharmaceutical compositions are given in a single or multiple doses per time period, for example, daily, weekly, bi-weekly, or monthly. For example, in some embodiments, the pharmaceutical compositions are given from one to four times per period.

In some embodiments, for superficial fungal infections of the skin, the present compositions with/or without glycerol and/or a retinoid are given once per week, for a period of from one to six weeks.

In some embodiments, for onychomycosis infections, the compositions with/or without glycerol and with/or without a retinoid are applied at a frequency of from one to four times daily, for a period of six weeks for infections of the fingernails or twelve weeks for infection of the toenails. This treatment may be repeated including for example, once daily, twice daily, three times daily, or four times daily, one a daily or weekly basis, or on a monthly or every other month schedule, for a period of time sufficient to alleviate symptoms or clear the fungal infection, for example, for a period of time from 1 to 52 weeks, from 1 to 26 weeks, from 26 to 52 weeks, from 13 to 39 weeks, from 20 to 40 weeks, from 20 to 48 weeks, from 5 to 50 weeks, from 10 to 45 weeks, from 15 to 40 weeks, from 20 to 35 weeks, from 25 to 30 weeks, for about 30 weeks; from 28 weeks to 50 weeks, from 30 week to 48 weeks, from 32 to 46 weeks, from 34 to 44 weeks, from 36 to 42 weeks, from 38 to 40 weeks, from 2 to 24 weeks, from 2 to 22 weeks, from 2 to 20 weeks, from 2 to 18 weeks, from 2 to 16 weeks, from 2 to 14 weeks, from 2 to 12 weeks, from 2 to 10 weeks, from 2 to 8 weeks, from 2 to 6 weeks, from 2 to 4 weeks, from 10 to 48 weeks, from 12 to 48 weeks, from 14 to 48 weeks, from 16 to 48 weeks, from 18 to 48 weeks, from 20 to 48 weeks, from 22 weeks to 48 weeks, from 24 week to 48 weeks, from 26 to 48 weeks, from 28 to 48 weeks, from 30 to 48 weeks, from 32 to 48 weeks, from 34 to 48 weeks, from 34 to 48 weeks, from 36 to 48 weeks, from 38 to 48 weeks, from 40 to 48 weeks, from 42 to 48 weeks, from 44 to 48 weeks, from 46 to 48 weeks, for 1 weeks, for 2 weeks, for 4 weeks, for 6 weeks, for 8 weeks, for 10 weeks, for 12 weeks, for 24 weeks, for 26 weeks, for 28 weeks, for 30 weeks, for 32 weeks, for 34 weeks, for 36 weeks, for 38 weeks, for 40 weeks, for 42 weeks, for 44 weeks, for 46 weeks, for 48 weeks, for 50 weeks, for 50 weeks, or for 52 weeks. For example, the present compositions can be topically administered, at a frequency of once per day for a period of time from 1 week to 52 weeks, for example for about from 24 weeks to 48 weeks.

In some embodiments, for onychomycosis infections the presently described compositions with/or without glycerol and with/or without a retinoid are applied in a therapeutically effective amount, for example, an amount sufficient to cover an affected area plus a margin of healthy skin and/or nail surrounding the affected area, for example, a margin of about 0.1 to about 0.5 inches. Suitable amounts per application per affected area or cumulative daily dosage per affected area is applied.

Two commercially available amino acid solutions that are used for intravenous administration and are approved by the food and drug administration (FDA) for this use were evaluated. Both have a similar composition of amino acids except that the second solution has three additional amino acids: Tyrosine, which has been found to have a neutral effect on biofilm, whereas the additional two amino acids Aspartic Acid and Glutamic Acid, were found to be very active against both bacterial and fungal biofilm. The first solution also had a very small concentration of the antibiofilm amino acid cysteine which was not present in the second solution. Both of these solutions were compared for their ability to compete against bacterial and fungal biofilms. The first solution was found to be very active against both bacterial and fungal biofilm whereas the second solution showed no activity against biofilm. The only other difference between the two solutions was the main source of calories used in these solutions. The first solution used 3% glycerol whereas the second solution used 5% dextrose as a source of additional calories. While glycerol on its own was not found to have antibiofilm effect, there was an effect that enabled antibiofilm amino acids to be more effective in combating biofilm and also attenuated the effect of amino acids that supported biofilm formation (pro-biofilm amino acids) while in the presence of glycerol.

The concentration of glycerol at the site of infection, during the first infusion, was elevated sufficiently to cause increased efficacy of antibiofilm amino acids in their ability to reduce the formation of bacterial and fungal biofilm and to reduce (destroy) already formed biofilm at the site of infection consistent with a loss in the ability of the infecting biofilm-forming microbes to maintain the preformed biofilm. The elevated concentration of glycerol was able to attenuate the pro-biofilm effect of pro-biofilm amino acids in their ability to aid in the formation of biofilm and in their ability to interfere with the antibiofilm effect of antibiofilm amino acids. This all indicates that the ability of the living microbes to support and maintain their biofilm is interfered with.

In animal species other than *Homo sapiens*, amino acids may be present in their blood other than the 32 that were examined for this patent. Likewise, human plasma that contains the 2 amino acid derivatives that were examined for this patent may have many other amino acid derivatives that have both antibiofilm and pro-biofilm effects. Many different amino acids and amino acid derivatives would be examined for their effect on bacterial and fungal biofilm and used appropriately in humans and also used in a species-specific way so as to avoid harmful toxic effects to animals and the environment. This/these amino acid(s) and the amino acid derivatives can be used to treat infections and contaminations on growing plants, on various surfaces such as walls in health care facilities, surfaces in food processing environments, on food stuff, in the unclogging and maintenance of pipes for water distribution and the distribution of other liquids and gases as required in commercial and manufacturing environments. They can be used topically on humans and also used as an aid in sterilizing surgical equipment or on solid or liquid surfaces and in the treatment of water for the safe use of water for animal consumption and in the irrigation of vegetation. These amino acids and amino acid derivatives can be aided by the presence of an appropriate concentration of glycerol. These compositions of amino acids, and/or amino acid derivatives, with or without glycerol can be applied once or twice in a 24 hour period and can include, for example, from about 0.001 grams to about 8 grams; from about 0.2 grams to about 4.5 grams; from about 0.3 grams to about 4 grams; from about 0.4 grams to about 3.5 grams; from about 0.4 grams to about 3 grams; from about 0.4 grams to about 2.5 grams; from about 0.4 grams to about 2 grams; from about 0.4 grams to about 1.5 grams; from about 0.5 grams to about 8 grams; from about 0.5 grams to about 6 grams; from about 0.5 grams to about 5 grams; from about 0.5 grams to about 4.5 grams; from about 0.5 grams to about 4 grams; from about 0.5 grams to about 3.5 grams; from about 0.5 grams to about 3 grams; from about 0.5 grams to about 2.5 grams; from about 0.5 grams to about 2 grams; from about 0.5 grams to about 1.5 grams; from about 0.5 grams to about 1 gram; from about 1 gram to about 8 grams; from about 1 gram to about 8 grams; from about 1 gram to about 7 grams; from about 1 gram to about 6 grams; from about 1 gram to about 5 grams; from about 1 gram to about 4.5 grams; from about 1 gram to about 4 grams; from about 1 gram to about 3.5 grams; from about 1 gram to about 3 grams; from about 1 gram to about 2.5 grams; from about 1 gram to about 2 grams; from about 1 gram to about 1.5 grams; from about 1.5 grams to about 8 grams; from about 1.5 grams to about 7 grams; from about 1.5 grams to about 6 grams; from about 1.5 grams to about 5 grams; from about 1.5 grams to about 4.5 grams; from about 1.5 grams to about 4 grams; from about 1.5 grams to about 3.5 grams; from about 1.5 grams to about 3 grams; from about 1.5 grams to about 2.5 grams; from about 1.5 grams to about 2 grams; from about 2 grams to about 8 grams; from about 2 grams to about 7 grams; from about 2 grams to about 6 grams; from about 2 grams to about 5 grams; from about 2 grams to about 4.5 grams; from about 2 grams to about 4 grams; from about 2 grams to about 3.5 grams; from about 2 grams to about 3 grams; from about 2 grams to about 2.5 grams; from about 2.5 grams to about 8 grams; from about 2.5 grams to about 7 grams; from about 2.5 grams to about 6 grams; from about 2.5 grams to about 5 grams; from about 2.5 grams to about 4.5 grams; from about 2.5 grams to about 4 grams; from about 2.5 grams to about 3.5 grams; from about 2.5 grams to about 3 grams; from about 3 grams to about 8 grams; from about 3 grams to about 7 grams; from about 3 grams to about 6 grams; from about 3 grams to about 5 grams; from about 3 grams to about 4.5 grams; from about 3 grams to about 4 grams; from about 3 grams to about 3.5 grams; from about 3.5 grams to about 8 grams; from about 3.5 grams to about 7 grams; from about 3.5 grams to about 6 grams; from about 3.5 grams to about 5 grams; from about 3.5 grams to about 4.5 grams; from about 3.5 grams to about 4 grams; from about 4 grams to about 8 grams; from about 4 grams to about 7 grams; from about 4 grams to about 6 grams; from about 4 grams to about 5 grams; from about 4 grams to about 4.5 grams; from about 4.5 grams to about 8 grams; from about 4.5 grams to about 7 grams; from about 4.5 grams to about 6 grams; from about 4.5 grams to about 5 grams; from about 5 grams to about 8 grams; from about 5 grams to about 7 grams; from about 5 grams to about 6 grams; from about 5.5 grams to about 8 grams; from about 5.5 grams to about 7 grams; from about 5.5 grams to about 6 grams; from about 6 grams to about 8 grams; from about 6 grams to about 7 grams; from about 6.5 grams to about 8 grams; from about 6.5 grams to about 7 grams; from about 7 grams to about 8 grams; from about 7.5 grams to about 8 grams; about 0.2 grams; about 0.5 grams; about 1 gram; about 1.5 grams; about 2 grams; about 2.5 grams; about 3 grams, about 3.5 grams; about 4 grams, about 4.5 grams; about 5 grams, about 5.5 grams; about 6 grams, about 6.5 grams; about 7 grams, about 7.5 grams; or about 8 grams.

In certain onychomycosis cases a maximum per application, per affected area, a is a dose of 8 grams of the presently described composition with or without glycerol and with or without a retinoid, is applied to an affected area (all nails), for example, once or twice daily. In some embodiments, the present composition is applied, for example once or twice daily, for example, morning and/or evening, for about 1-52 weeks. For example, in some embodiments, the presently described compositions are topically applied in an amount sufficient to cover an affected area plus a margin of healthy skin and/or nail surrounding the affected area, for example, a margin of about 0.1 to about 0.5 inches, at a frequency, for example, of once a day, for a time period, for example of about 24 to about 48 weeks.

Glycerol Composition for Treating Microbial Biofilms by the Use of Glycerol on Microbes All of the above information with respect to glycerol is incorporated and applicable to this section of the application. Disclosed are compositions for the reduction/removal of biofilm that is produced by biofilm-forming microbes that are infecting or contaminating plants, or contaminate inanimate surfaces such as in medical facilities, food processing environments, manufacturing facilities, pipes that are used for the transport of water or other fluids and/or gases, etc., which would enable sterilizing agents and/or antimicrobials to get better access to the offending microbes once the protection of the biofilm has been removed.

Glycerol has a direct effect on the infecting microbes that enables the plasma amino acids and amino acids derivatives to change the physiology of the microbe so that it stops making biofilm and initiates destruction of the already formed biofilm.

The concentration of glycerol in plasma is normally low and does not adversely affect the ability of pro-biofilm amino acids to aid microbes in making biofilm. The pro-biofilm amino acids dominate over the antibiofilm amino acids and amino acid derivatives.

When plasma Glycerol is increased to a sufficient concentration the pro-biofilm effect on microbes by pro-biofilm amino acids and amino acid derivatives is attenuated and allows antibiofilm amino acids and amino acid derivatives to become dominant.

In an additional embodiment, the present invention is directed to compositions and methods of infusing a sufficient amount of glycerol into the vascular system of animals including humans in order to produce a sufficient concentration of plasma glycerol that in turn sensitizes the infecting microbes to antibiofilm amino acids and amino acid derivatives.

In situations where the biofilm is not bathed in plasma, such as in an infected cutaneous ulcer, the microbe produces an attractant that attracts the Glycerol and then the antibiofilm amino acids to the microbe through the fluid contained in the infection.

EXAMPLES

Example 1: Patient Study

A 66-year-old female who developed cellulitis and an open ulcer on her leg was treated with oral antibiotics at an outpatient wound care center. When the outpatient care was not successful in treating her, she was admitted to the hospital for intravenous antibiotics. After 3 weeks of this treatment, there was no sign of improvement and the ulcer was enlarging. At this time, the ulcer measured 3 centimeters by 1.5 centimeters in size and there was surrounding redness consistent with inflammation. With the consent of the patient, she was given an intravenous infusion that had been used for many years for nutritional purposes. It consisted of 3% glycerol and 3% amino acids. The infusion was given at a rate of 80 ml per hour. After 48 hours of this infusion, there was evidence that the ulcer was healing and the adjacent inflammatory response was abating. After 72 hours the intravenous antibiotics were discontinued and the patient was discharged home on oral antibiotics. When she was reexamined a few weeks later there was no evidence of the ulcer and the localized redness had cleared. The inventor has found that such infected ulcers are difficult to treat with antimicrobials (e.g., antibiotics) because the ulcers have developed a bacterial biofilm that provides tolerance to the antimicrobial agents and the immune system.

The composition of this infusion (first composition) comprised a solution of 15 amino acids: Alanine 0.21 g %, Arginine 0.29 g %, Cysteine<0.014 g %, Glycine0.42 g %, Histidine0.085 g %, Isoleucine 0.21 g %, Leucine 0.27 g %, Lysine(asLysineAcetateUSP0.31 g) 0.22 g %, Methionine 0.16 g %, Phenylalanine 0.17 g %, Proline 0.34 g %, Serine 0.18 g %, Threonine 0.12 g %, Tryptophan 0.046 g %, Valine 0.2 g %. It also comprised 3% Glycerol as a source of extra calories. All of the amino acids were L-Isomers except Glycine which does not have an isomer.

A request was made that in vitro testing be conducted with the above-mentioned composition to check on its ability to compete against bacterial and fungal biofilm. The composition was found to be effective in the inhibition of the formation of biofilm by biofilm-forming bacteria. This composition was also capable of destroying the preformed biofilm that had been constructed by biofilm-forming bacteria and fungi.

A further request was made that another composition which was also used for intravenous feeding, be tested for its effect against bacterial and fungal biofilm. The compositions of the two infusions comprised 14 amino acids that were similar. After doing in vitro testing on the amino acids later, it was found that 12 of the 14 supported bacteria in forming biofilm (pro-biofilm amino acids). One (valine) supported the formation of biofilm made by biofilm-forming fungi (pro fungal biofilm amino acid). One (Histidine) was neutral, having no effect on biofilm. The initial composition also comprised Cysteine that later was found to have an effect on both bacteria and fungi that make biofilm in that it causes these microbes to stop their formation of biofilm and to trigger these microbes to initiate destruction of the preformed biofilm. The L-Cysteine was at a very low concentration of <0.014%. When it was tested on its own later, it was found to have a potent antibiofilm effect on biofilm-forming bacteria and fungi with a maximum effect at a concentration of 0.5% and a rapid falling off in antibiofilm efficacy as its concentration decreased. The concentration of 0.5% was approximately 36 times the concentration of L-Cysteine that was present in the first composition. Cysteine was not present in the second composition.

A further request was made for another composition which was also used for intravenous feeding. This was also to be tested for its effect against bacterial and fungal biofilm. The compositions of the two infusions comprised 14 amino acids that were similar. After doing in vitro testing on the amino acids later it was found that 12 of the 14 supported bacteria in forming biofilm (pro-bacterial biofilm amino acids). One (valine) supported the formation of biofilm made by biofilm-forming fungi (pro-fungal biofilm amino acid) but had a dual function. Without the presence of a therapeutic concentration of glycerol its effect supported the formation of fungal biofilm (pro-biofilm amino acid). When in the presence of a therapeutic concentration, its antibacterial biofilm effect became dominant. One (Histidine) was neutral, having no effect on biofilm. The initial composition also comprised Cysteine that later was found to have an effect on both bacteria and fungi that make biofilm. It causes these microbes to stop their formation of biofilm and to trigger these microbes to initiate destruction of the pre-formed biofilm. The L-Cysteine was at a very low concentration of <0.014%. When it was tested on its own later, it was found to have a strong antibiofilm effect on biofilm-forming bacteria and fungi with a maximum effect at a concentration of 0.5% and a rapid falling off in antibiofilm efficacy as its concentration decreased. The concentration of 0.5% was approximately 36 times the concentration of L-Cysteine in the first composition. Cysteine was not present in the second composition. The composition of the second infusion had, in addition to the 14 amino acids that were also present in the first composition, 3 additional amino acids. One of these, tyrosine, was found to be neutral, having no effect on biofilm. The other two amino acids, Aspartic acid 0.49%, and Glutamic acid 0.517% were later found to have a strong effect on biofilm-forming bacteria and fungi in reducing biofilm formation and also causing these microbes to destroy their preformed biofilm. Their ideal concentration for antibiofilm effects was 0.5% for each on its own. They comprised 2 of the 3 most potent antibiofilm amino acids that are found in plasma. The third of these was L-Cysteine. These 3 potent antibiofilm amino acids, while each was at a concentration of 0.5%, produced a 50% or more decrease in the ability of biofilm-forming bacteria and fungi to produce new biofilm, whereas other antibiofilm amino acids and anti-biofilm amino acid derivatives produced a 30% or less decrease. When these three amino acids are combined, they have been found to have synergism with a marked potency on biofilm-forming bacteria and fungi. They cause the biofilm-forming bacteria and fungi to decrease biofilm formation by 90% and almost total elimination of preformed biofilm by the biofilm-forming bacteria and fungi. See and Tables B and C in parent application Ser. No. 18/160,559.

Despite this when Cysteine was added to Aspartic acid and Glutamic acid in the second composition there was no evidence of any effect against biofilm until the concentration of Cysteine reached 0.4% which was approximately 29 times the concentration of Cysteine in the first composition.

At this time the second composition became successful at hindering fungal biofilm formation but had no effect on bacterial biofilm. The 12 pro-bacterial biofilm amino acids and the one pro-fungal biofilm amino acid that normally, over the eons, aided the formation of bacterial biofilm by bacterial microbes and fungal microbes in forming biofilm were present in both compositions. These pro-biofilm amino acids were able to nullify the strong antibiofilm effect on these microbes that would be expected from the synergism of Aspartic acid, L-Cysteine, and Glutamic acid in the second composition. The one pro-fungal amino acid that was present in the second composition and that was able to aid the formation of fungal biofilm eventually succumbed to the potent antibiofilm trio when the concentration of L-Cysteine reached 0.4%. Each of the two compositions comprised the same 13 pro-biofilm amino acids that help the bacteria and fungi in forming biofilm in the second composition. In the first composition, these 13 pro-biofilm amino acids became inactive in their pro-biofilm effect because of the presence of the artificially high glycerol concentration which inactivated their pro-biofilm effect. The first composition did not contain the potent trio of antibiofilm amino acids that were present in the second composition after the addition of Cysteine at a concentration of 0.4%. Nevertheless, the first composition was capable of preventing fungal and bacterial biofilm formation by fungal and bacterial biofilm-forming microbes and was also capable of initiating the destruction of the preformed biofilm that was present due to the effect of a sufficient concentration of glycerol in this composition and also the increased microbial sensitivity to antibiofilm amino acids while in the presence of a sufficient concentration of glycerol.

In summary, the second composition was incapable of having the bacteria or the fungi stop making new biofilm. It was also unable to initiate destruction of pre-formed biofilm. In vitro studies later showed that the 13 amino acids that were present in second infusion aided bacteria and fungi in the production of biofilm. When Cysteine at a 0.4% concentration was added to this composition it became capable of having the fungi stop forming new biofilm and initiated the fungi to start destruction of pre-formed fungal biofilm but had no influence on the biofilm being formed by bacteria.

The first composition comprised 3% glycerol whereas the second composition comprised 5% dextrose as an additional source of calories.

The second composition had no effect on biofilm on in vitro testing prior to the addition of Cysteine 0.4%. After the addition of Cysteine was done the second composition developed an antibiofilm effect against fungal biofilm but not against bacterial biofilm. These 2 compositions had 14 amino acids that were similar.

As mentioned above, the composition of both infusions comprised 12 amino acids that later were found to support bacterial biofilm formation (pro-bacterial biofilm amino acids). One of the amino acids, Valine, supported fungal biofilm formation (pro-fungal biofilm amino acid) while not being influenced by the raised concentration of glycerol. One was neutral (Histidine). This accounted for the shared 14 amino acids.

The first (initial) composition had only 1 amino acid, L-Cysteine <0.014%, that had an anti-fungal biofilm effect. This was approximately $\frac{1}{36}$ of the ideal concentration for anti-biofilm effect that was found on in vitro testing while in the absence of glycerol.

The first composition, while in the presence of a sufficient concentration of glycerol. and with only two anti-bacterial amino acids were able to overcome the pro-biofilm properties of the 13 pro-bacterial biofilm amino acids which included valine. As is explained above and shown in Table D some amino acids have a dual effect, this includes Valine which has a dual pro-fungal biofilm effect and an anti-bacterial biofilm effect. While under the influence of a therapeutic concentration of glycerol the pro-fungal biofilm effect is attenuated which allows the anti-bacterial biofilm effect to be active. This therefore would increase the anti-bacterial biofilm amino acids to 2 which are L-Cysteine and Valine. The in vitro study of the effect of the first solution on fungi shows that a very low concentration of L-Cysteine was able to cease biofilm formation and caused destruction of already formed biofilm.

The anti-biofilm amino acids and amino acid derivatives initiate a trigger in these microbes to begin premature destruction of their biofilm which would allow the newly formed microbes to be released into the blood as planktonic microbes without protection of biofilm where they would be vulnerable to attack by the immune system and the administered antimicrobial. This phenomenon of releasing planktonic (free floating) microbes into the blood is the means by which these infections spread in the body. Once they attach to new surfaces through Van der Waal forces they get busy multiplying and making new biofilm colonies. In normal plasma there is glycerol present but is at a sufficiently low concentration to have no effect on the plasma antibiofilm amino acids or on the antibiofilm amino acid derivatives ability to affect the infecting microbes. When the plasma glycerol concentration is kept sufficiently elevated these planktonic microbes are unable to form new biofilm and are vulnerable to attack by the immune system and an administered antimicrobial. Thus, the first composition, while in the presence of an adequate concentration of glycerol, was able to attenuate the 13 pro-biofilm amino acids and was also aided by the very low concentration of Cysteine ($\frac{1}{36}$ of its ideal concentration on in vitro testing) which allowed the Cysteine to become dominant over the 12 pro-bacterial biofilm amino acids.

The second composition did not contain glycerol. This allowed the pro-biofilm amino acids to be dominant despite the presence of two antibiofilm amino acids which were active against both bacterial and fungal biofilm. These were Aspartic acid and Glutamic acid, wherein each respectively was at a concentration of 0.49 and 0.517 g %. The ideal concentration of each of these, while in the absence of glycerol on in vitro testing has been found to be 0.5 g %. The second composition had no antibiofilm effect on in vitro testing. When the second composition had L-Cysteine, at a concentration of 0.4 g % added, they developed an antibiofilm property against fungal biofilm but not against the bacterial biofilm. This new composition was able to inhibit the single pro-fungal biofilm amino acid (Valine) that was present but had no effect on the 12 pro-bacterial biofilm amino acids that were present. The second composition maintained dominance of the pro-biofilm amino acids when not affected by a high glycerol concentration. The other difference between these compositions was the 3 g % of glycerol that was present in the first composition and the 5 g % of dextrose that was present in the second composition as an additional source of calories.

In summary, composition no. 1 had 12 amino acids that supported bacterial biofilm. and one neutral amino acid. It also comprised one anti-biofilm amino acid, L-Cysteine, with activity against both bacterial and fungal biofilm though it was at $\frac{1}{36}$ of its ideal antibiofilm concentration on in vitro testing while in the absence of glycerol. It also comprised 3 g % glycerol. It had a dual amino acid, Valine, that in the presence of the therapeutic concentration of Glycerol had an anti-bacterial biofilm effect and lost its pro-fungal biofilm effect.

Composition no. 2 had the same 12 amino acids that supported bacterial biofilm and the same one amino acid that supported fungal biofilm and two neutral amino acids. It also comprised 2 additional antibiofilm amino acids, Aspartic acid and Glutamic acid, which had similar antibiofilm activity to L-Cysteine but were at close to their ideal concentrations for antibiofilm activity that was found on in vitro testing. However, initial in vitro testing showed this composition had no adverse effect on bacterial or fungal biofilm. When L-Cysteine was added to composition no. 2 it had no effect against biofilm until the added L-Cysteine concentration reached 0.4% wherein it developed a reduction in biofilm formation and an onset of biofilm degeneration by fungi but had no influence on reducing bacterial biofilm formation or already formed biofilm despite the synergism that would be expected to occur when the 3 of these antibiofilm amino acids were combined. The second composition maintained dominance over the antibiofilm amino acids.

The reason for the large increase in antibiofilm effect in composition no. 1 was the presence of a raised concentration of glycerol.

This showed that when in the presence of a sufficient concentration of glycerol a change in the physiology of the infecting biofilm forming microbes which lost sensitivity to pro-biofilm amino acids and an increased sensitivity to anti biofilm amino acids and amino acid derivatives which resulted in the destruction of preformed biofilm and a reduction in biofilm formation.

The ability of the biofilm-forming microbes to form new biofilm and to protect already formed biofilm was adversely affected by the first composition.

The second composition demonstrated the dominance of pro-biofilm amino acids over the antibiofilm amino acids when there was an insufficient concentration (absence) of glycerol. This is also what occurs in normal plasma where a supportive environment to infecting biofilm-forming microbes is found while in the presence of a low concentration of glycerol that is insufficient to have an effect on plasma amino acids and amino acid derivatives.

The concentration of glycerol that is normally found in plasma varies between 0.00046 and 0.00092 g % (0.05 and 0.1 mmol/L) but this concentration, over the eons, has been insufficient to aid the antibiofilm amino acids and the antibiofilm amino acid derivatives that are present in plasma to overcome the pro-biofilm amino acids and the pro-biofilm amino acid derivatives that are also present in plasma and that are able to support the formation of biofilm by infecting biofilm-forming microbes while awash in the natural(usual) concentration of plasma glycerol. This has allowed a direct benefit to pathological biofilm-forming microorganisms while infecting animals including humans.

By increasing the concentration of glycerol sufficiently in the plasma of the treated patient, as occurred with the infusion of the first composition, the plasma antibiofilm amino acids and amino acid derivatives that normally have had no effect on biofilm, caused the infecting bacteria to lose the help they had received in making new biofilm with the aid of the pro-biofilm amino acids and amino acid derivatives prior to receiving the glycerol infusion. The boost that the pro-biofilm amino acids and the pro-biofilm amino acid derivatives had given to the bacteria while they were establishing themselves for weeks in the infected ulcer, abated, once the composition which included glycerol was being infused into her plasma. The pro-biofilm amino acids and the pro-biofilm amino acid derivatives ability to continue helping the bacteria to form new biofilm became attenuated due to the effect of the increase in plasma glycerol concentration. In addition to this the increased effectiveness of the once ineffective antibiofilm amino acids and antibiofilm amino acid derivatives due to the glycerol effect on the bacteria stopped the bacteria from making new biofilm and initiated the destruction of the preformed biofilm. This led to a rapid loss of protection for the denuded bacteria which led to the decimation of the unprotected bacteria by the administered antibiotic and her immune system.

By increasing the concentration of the plasma glycerol the antibiofilm amino acids and the antibiofilm amino acid derivatives were able to dominate the pro-biofilm amino acids and amino acid derivatives and thus were able to conquer the biofilm that was present in the patients infected leg ulcer. This has not occurred during the hundreds of million years that bacteria have been infecting animals.

Though infusing the first composition into the patient's plasma raised the concentration of certain pro-biofilm amino acids in the patient's plasma, they were unable to aid in the production of biofilm by the infecting bacteria.

The first composition had a glycerol concentration of 3 g/100 ml. It was infused at a rate of 80 ml/hour. This would infuse 2.4 g of glycerol into her blood each hour. Her blood would have approximately 3 liters of plasma. Thus, one liter of plasma would receive 0.8 grams of glycerol each hour which would translate to 0.08 g/100 ml/hour or 0.04 g/100 ml of plasma per hour. The concentration of glycerol at the site of infusion would be approximately 83 to 166 times the amount of glycerol that was present in the venous plasma at the site of infusion prior to the infusion. This venous blood glycerol is further diluted on its way to the heart and further diluted when pumped out in the arterial system. Glycerol is nontoxic at the concentration used in the patient. There is a wide range between the therapeutic and toxic concentrations. Checking arterial glycerol concentrations would be impractical under clinical conditions resulting in an infusion amount based on clinical experience.

Table D shows which plasma amino acids and amino acid derivatives have pro-bacterial biofilm and pro-fungal biofilm effect, anti-bacterial biofilm effect and anti-fungal biofilm effect, and those with a dual effect.

The addition of a sufficient concentration of Glycerol was able to change the balance of power in the patient's plasma in favor of antibiofilm amino acids and antibiofilm amino acid derivatives which caused a negative effect on the ability of the infecting bacteria in their effort to make new biofilm and to maintain already formed biofilm and also trigger a programmed destruction of the biofilm.

The patent applicant claims that the new and significant changes that occur in the biofilm forming microbes as a result of the elevation in the concentration of glycerol that is in contact with the microbes to lose sensitivity to probiofilm amino acids and increase sensitivity to antibiofilm amino acids and amino acid derivatives. See Table D. See Table D.

However, it was found that at a therapeutically acceptable concentration, glycerol had a positive effect on the ability of the antibiofilm amino acids and amino acid derivatives to act on the infecting bacteria, causing inhibition in their ability to produce new biofilm and in their ability to protect already formed biofilm from premature destruction.

The increased concentration of glycerol also had a negative effect on the ability of the pro-biofilm amino acids to dominate over the anti-biofilm amino acids and amino acid derivatives and in the ability of the pro-biofilm amino acids to aid the bacteria and fungi in biofilm formation.

The 32 amino acids that were examined comprised nontoxic, non-bonded amino acids comprising aspartic acid, cysteine, glutamic acid, alanine, beta-alanine, 2-aminoadipic acid, 2-aminobutyric acid, arginine, asparagine, citruline, cystathionine, glycine, glutamine, histidine, homocysteine, hydroxyproline, isoleucine, leucine, lysine, methionine, 1-methyl-histidine, 3-methyl-histidine, ornithine, phenylalanine, phosphoserine, proline, serine, taurine, threonine, tryptophan, tyrosine, and valine.

All of the amino acids were the L-Isomers except for Glycine which does not have an isomer. See Table D.

The 2 non-bonded, non-toxic, amino acid derivatives that were tested comprised ethanolamine and phosphoethanolamine. See* in Table D The 32 amino acids and the 2 amino acid derivatives were evaluated for their effect in both the inhibition of formation and in the reduction (destruction) of bacterial and fungal biofilm. These amino acids and the amino acid derivatives were also tested for their ability to promote the formation of biofilm (pro-biofilm) and in their neutral or absent effect on biofilm. See Table D.

Of the 34 molecules tested, ten amino acids and two amino acid derivatives (a total of 12) were found to have an antibiofilm effect. Three of these amino acids were more potent than the other seven amino acids and the two amino acid derivatives with >than 50% potency in each of the three amino acids versus 30% or less potency in each of the less potent seven amino acids and the two amino acid derivative on the inhibition of formation and on the destruction of both bacterial and fungal biofilm.

The 3 potent antibacterial and antifungal biofilm amino acids comprised Aspartic acid, Cysteine, and Glutamic acid, and when combined, demonstrated synergism with a 90% inhibition of biofilm formation and a nearly complete elimination of preformed biofilm under experimental conditions which was made without the presence of glycerol or other amino acids or their derivatives.

When under the influence of a sufficient concentration of Glycerol, amino acids and amino acid derivatives with dual function e.g., antibacterial biofilm effect and pro-fungal biofilm effect or vice versa, the pro-biofilm effect is reduced (attenuated) and the antibiofilm effect becomes enhanced.

9 amino acids comprising Beta-Alanine, 2-Amino Adipic acid, Aspartic acid, Cystathionine, Cysteine, Glutamic acid, Hydroxyproline, 3-Methylhistidine, and Phosphoserine, have antibacterial biofilm effect. One amino acid derivative, Phosphoethanolamine also has antibacterial biofilm effect for a total of 10. See Table D.

6 amino acids comprising Aspartic acid, Cysteine, Glutamic acid, Homocysteine, Hydroxyproline, and Phosphoserine have antifungal biofilm effects. One amino acid derivative, Ethanolamine, also had an antifungal biofilm effect for a total of 7

Sixteen amino acids comprising alanine, arginine, asparagine, citrulline, glycine, isoleucine, leucine, lysine, methionine, phenyalanine, ornithine, proline, serine, taurine, threonine, and tryptophan, promoted bacterial biofilm formation (probacterial biofilm amino acids). See Table D.

Two amino acids comprising 3-Methylhistidine and Valine promoted fungal biofilm formation.

Sixteen of the examined molecules comprising fifteen amino acids and one amino acid derivative were found to be neutral on either the inhibition or the reduction(destruction) assay. 10 of the 16 were neutral on the inhibition assay. 12 were neutral on the destruction assay. 5 were found to be neutral on testing with both assays. Because of the different effects that were seen on the inhibition and the destruction (reduction) assays the author suggests looking at Table D.

The amino acids and the amino acid derivatives that inhibit formation and/or reduction/destruction of biofilm by the biofilm-forming microbes will be referred to as antibiofilm amino acids and antibiofilm amino acid derivatives or else otherwise defined. The amino acids and the amino acid derivatives that promote biofilm formation by the biofilm-forming microbe will be referred to as pro-biofilm amino acids and pro-biofilm amino acid derivatives or else otherwise defined. The amino acids and the amino acid derivatives that do not have an effect on biofilm will be referred to as neutral or else otherwise defined.

Example 2: Method of Investigation

Two types of biofilm assays were performed: an inhibition assay and a disruption assay. The inhibition assay assesses the compound's ability to prevent biofilm development, while the disruption assay assesses the compound's ability to break up an existing mature biofilm.

For fungal biofilm assays, all solutions were prepared in RPMI 1640 medium. All bacterial biofilm solutions were prepared in Tryptic Soy Broth (TSB), supplemented with 1% glucose (henceforth referred to as TSB-G). All subsequent procedures were performed in a manner that maintained sterility. A solution of each amino acid or an amino acid derivative to be tested was prepared in weight to volume concentrations ranging from 0.1-5.0%. Amino acids and amino acid derivatives were also tested in combinations. Compound solutions were homogenized with gentle agitation in the dark (4° C., 24 hours) before use.

32 Amino acids and 2 amino acid derivatives of the amino acid serine that occur freely in human blood were tested. The 32 amino acids that were tested comprise the following: L-alanine, Beta-alanine, 2-aminoadipic acid, 2-aminobutyric acid, L-arginine, L-asparagine, L-aspartic acid, L-citrulline, L-cysteine, L-glutamic acid, L-glycine, L-glutamine, L-histidine, 3-methyl-L-histidine, L-homocysteine L-isoleucine, L-leucine, L-lysine, L-methionine, L-ornithine, L-phenylalanine, L-proline, Trans-4-hydroxy-L-proline, L-serine, O-phospho-L-serine, L-taurine, L-threonine, L-tryptophan, L-tyrosine, and L-valine. Two amino acids (1-methyl-L-histidine and L-cystathionine) were prepared at the highest concentration of 0.2% due to their limited solubility. 31 of the 32 amino acids that were tested were the L-Isomers. Glycine has no stereoisomers. The 2 amino acid derivatives, ethanolamine and phosphoethanolamine were also tested. All biofilm assays were performed using 384-well non-tissue culture-treated polystyrene plates. The fungal species tested are as follows: *Candida albicans, Candida guilliermondii, Candida parapsilosis, Candida glabrata, Candida tropicalis* and *Candida* dubliniensis. The bacterial species tested are as follows: Staphylococci (standard wild type and methicillin-resistant strain USA300), *Escherichia coli, Pseudomonas aeruginosa* and *Staphylococcus epidermidis.*

Fungal strains were streaked on Yeast Peptone Dextrose (YPD) agar plates and incubated at 30° C. for 48 hours. A single colony from each strain to be tested was inoculated into YPD broth and grown for 12 hours at 30° C., shaking at 225 rpm. For the fungal biofilm inhibition assay, 1 μl of saturated overnight cell culture was added to either 80 μL of RPMI-1640 or RPMI-1640 supplemented with the amino acid compound solution to be tested, in a 384-well plate. The cells were allowed to adhere to the plate for 90 minutes at 37° C. with shaking (350 rpm). Loosely bound cells were washed once with phosphate-buffered saline (PBS) and 80 ul of RPMI-1640, or RPMI-1640 supplemented with the amino acid compound solution was added to the plate. The plate was further incubated for 24 hours at 37° C. with shaking (350 rpm). Media was carefully aspirated and the biofilm was measured by optical density at 600 nm. Twelve replicates were performed for each tested condition and the reported values are normalized to the control (RPMI-1640 media only). For the fungal biofilm disruption assays, 80 μL of RPMI-1640 was added to the plate, along with 1 μL of overnight cell culture. The cells were allowed to adhere to the plate for 90 minutes at 37° C. with shaking (350 rpm). Loosely bound cells were washed once with PBS and 80 μL of RPMI-1640 was added to the plate. The plate was further incubated for 24 hours at 37° C. with shaking (350 rpm). Media was carefully aspirated from the mature biofilm and 80 μL of RPMI-1640, or RPMI-1640 supplemented with the amino acid compound solution to be tested, was gently added to the plate. The plate was further incubated for 24 hours at 37° C. with shaking (350 rpm). Media was carefully aspirated, and the biofilm was measured by optical density at 600 nm. Twelve replicates were performed for each tested condition and the reported values are normalized to the control (RPMI-1640 media only).

Bacterial strains were streaked on Blood Agar plates (5% sheep blood in Tryptic Soy Broth) and incubated at 37° C. for 24 hours. A single colony from each strain to be tested was inoculated in a TSB broth and grown for 12 hours, at 37° C. with shaking (225 rpm). For the bacterial biofilm inhibition assays, 1 μL of saturated overnight cell culture was added to either 80 μL of TSB-G, or TSB-G supplemented with the amino acid compound solution to be tested, in a 384-well plate. The cells were allowed to adhere to the plate for 60 minutes at 37° C. without shaking. The media was carefully aspirated and 80 μL of TSB-G, or TSB-G supplemented with the amino acid compound solution was added to the plate. The plate was further incubated for 24 hours at 37° C. without shaking. Media was carefully aspirated and the biofilm was measured by optical density at 600 nm. Eight or twelve replicates were performed for each tested condition and the reported values are normalized to the control (TSB-G media only). For the bacterial biofilm disruption assays, 80 L of TSB-G was added to the plate, along with 1 μL of overnight cell culture. The cells were allowed to adhere to the plate for 60 minutes at 37° C. with no shaking. The media was carefully aspirated and 80 μL of TSB-G was added to the plate. The plate was further incubated for 24 hours at 37° C. with no shaking. Media was carefully aspirated from the mature biofilm and 80 μL of TSB-G, or TSB-G supplemented with the amino acid to be tested, was gently added to the plate. The plate was further incubated for 24 hours at 37° C. without shaking. Media was aspirated and the biofilm was measured by optical density at 600 nm. Twelve replicates were performed for each tested condition and the reported values are normalized to the control (TSB-G media only).

Results: Weight-to-volume concentrations ranging from 0.1-5.0% were tested for all amino acids and amino acid derivatives individually and in combination. The solution found to best abolish both fungal and bacterial biofilms is: 0.5% Cysteine+0.5% Glutamic Acid+0.5% Aspartic Acid. See Tables B and C.

Although these three amino acids individually have some anti-biofilm effects on fungal and bacterial biofilms on their own (biofilm formation is decreased on average by twofold or 50% for each), in combination, the effects are significantly increased (biofilm formation is decreased by tenfold or 90%}. This tenfold decrease in biofilm formation and the almost complete removal of the already formed biofilm indicates clear anti-biofilm synergy between these three amino acids when applied in combination. At concentrations lower than 0.5% of each amino acid, the biofilm inhibition and disruption rates are less effective. At concentrations above 0.5%, there is no increase, and there is a gradual decrease in effectiveness against biofilms (see Table B for C. Albicans data and Table C for S. aureus data). The same holds true for all species of microbes tested.

The other amino acids and the amino acid derivatives were tested for synergism but failed to show evidence of synergism at different combinations.

TABLE B

Biofilm Inhibition and Disruption Assays for *C. albicans* Fungus.

| Condition | Biofilm Remaining (Inhibition) | Biofilm Remaining (Disruption) |
|---|---|---|
| RPMI Medium | 1 | 1 |
| 0.5% L-cysteine + 0.5% L-glutamic acid + 0.5% L-aspartic acid | 0.1 +/− 0.04 | 0.03 +/− 0.03 |
| 0.4% L-cysteine + 0.4% L-glutamic acid + 0.4% L-aspartic acid | 0.4 +/− 0.08 | 0.3 +/− 0.05 |
| 2% L-cysteine + 2% L-glutamic acid + 2% L-aspartic acid | 0.2 +/− 0.06 | 0.07 +/− 0.01 |

TABLE C

Biofilm Inhibition and Disruption Assays for *S. Aurius* Bacterium.

| Condition | Biofilm Remaining (Inhibition) | Biofilm Remaining (Disruption) |
|---|---|---|
| TSB-G Medium | 1 | 1 |
| 0.5% L-cysteine + 0.5% L-glutamic acid + 0.5% L-aspartic acid | 0.1 +/− 0.04 | 0.2 +/− 0.07 |
| 0.4% L-cysteine + 0.4% L-glutamic acid + 0.4% L-aspartic acid | 0.3 +/− 0.05 | 0.5 +/− 0.04 |
| 2% L-cysteine + 2% L-glutamic acid + 2% L-aspartic acid | 0.2 +/− 0.09 | 0.3 +/− 0.06 |

Table D summarizes the results of the inhibition assay and the destruction assay, promotion, and neutral effect of the 32 amino acids and the 2 amino acid derivatives tested on bacterial (*S. aureus*) biofilm and fungal biofilm (*C. albicans*).

Each of the 32 amino acids and the 2 amino acid derivatives were tested against bacterial (*S. aurius*) biofilm formation and against fungal (*C. albicans*) biofilm formation (inhibition assay) and also in a destruction assay.

The results of the reduction(destruction) and the inhibition assays are frequently different, as can be seen in Table D.

TABLE D

| | Reduce or Inhibit B Biofilm | Reduce or Inhibit F Biofilm | Promote B Biofilm | Promote F Biofilm | Reduce Both | Promotes Both | Neutral |
|---|---|---|---|---|---|---|---|
| Alanine | | ● | | | | | ■ |
| Beta-Alanine | ■ | | | | | | ● |
| 2 Aminoadipic Acid | ●■ | | | | | | |
| 2 Aminobutyric Acid | | | | | | | ●■ |
| Arginine | | | ●■ | | | | |
| Asparagine | | | | ■ | | | ● |
| Aspartic Acid | ●●■■ | ●●■■ | | | ●●■■ | | |
| Citrulline | | | | ●■ | | | |
| Cystathionine | ● | | | | | | ■ |
| Cysteine | ●●■■ | ●●■■ | | | ●●■■ | | |
| Ethanolamine* | | ■ | | | | | ● |
| Glutamine | | | | | | | ●■ |
| Glutamic Acid | ●●■■ | ●●■■ | | | ●●■■ | | |

TABLE D-continued

| | Reduce or Inhibit B Biofilm | Reduce or Inhibit F Biofilm | Promote B Biofilm | Promote F Biofilm | Reduce Both | Promotes Both | Neutral |
|---|---|---|---|---|---|---|---|
| Glycine | | | ●■ | | | | |
| Histidine | | | | | | | ●■ |
| Homocysteine | | ●■ | | | | | |
| Hydroxyproline | ●■ | ■ | | | | | |
| Isoleucine | | | ●■ | | | | |
| Leucine | | | ●■ | | | | |
| Lysine | | | ●■ | | | | |
| Methionine | | | ■ | | | | ● |
| 1-Methylhistidine | | | | | | | ●■ |
| 3-Methylhistidine | ● | | | ●■ | | | |
| Phenylalanine | | | ●■ | | | | |
| Ornithine | | | ● | | | | ■ |
| Phospho-ethanolamine* | ●■ | | | | | | |
| Phosphoserine | ● | ● | | | | | ■ |
| Proline | | | ● | | | | |
| Serine | | ● | ● | | | | |
| Taurine | | | ● | | | | |
| Threonine | | ● | ● | | | | |
| Tryptophan | | ● | ● | | | | |
| Tyrosine | | | | | | | ● |
| Valine | ● | | ● | | | | |

*The two amino acid derivatives are identified by an asterisk.

Table D. Single dot [ie. ●] signifies little effect on the Disruption Biofilm Assay (from about 10 to less than 30%). Two dots [ie. ●●] signifies a major effect (greater than about 50%), on the Disruption Biofilm Assay. Single square [ie. ■] signifies little effect on the Inhibition Biofilm Assay (from about 10 to less than 30%). Two squares [ie. ■■] signifies a major effect (greater than about 50%), on the Inhibition Biofilm Assay. B Biofilm=Bacterial Biofilm; F Biofilm=Fungal Biofilm; Neutral=no effect on the biofilm.

There was evidence of synergism when Aspartic acid and Cysteine and Glutamic acid were combined. The other amino acids and the amino acid derivatives did not show evidence of synergism when examined in various combinations. (See Tables B and C).

Because of the various effects on biofilm by different amino acids and the amino acid derivatives that were examined, the present format Tables D, E, & F are the best way to present the findings.

TABLE E

Pro-biofilm amino acids and amino acid derivatives that have an effect on microbes and cause an increase in biofilm formation by the microbes while in the absence of an infusion of glycerol.

| | Reduce or Inhibit B Biofilm | Reduce or Inhibit F Biofilm | Promote B Biofilm | Promote F Biofilm | Reduce Both | Promotes Both | Neutral |
|---|---|---|---|---|---|---|---|
| Alanine | | | ● | | | | ■ |
| Beta-Alanine | | | | | | | ● |
| 2 Aminoadipic Acid | | | | | | | |
| 2 Aminobutyric Acid | | | | | | | ●■ |
| Arginine | | | ●■ | | | | |
| Asparagine | | | ■ | | | | ● |
| Aspartic Acid | | | | | | | |
| Citrulline | | | ●■ | | | | |
| Cystathionine | | | | | | | ■ |
| Cysteine | | | | | | | |
| Ethanolamine* | | | | | | | ● |
| Glutamine | | | | | | | ●■ |
| Glutamic Acid | | | | | | | |
| Glycine | | | ●■ | | | | |
| Histidine | | | | | | | ●■ |
| Homocysteine | | | | | | | |
| Hydroxyproline | | | | | | | |
| Isoleucine | | | ●■ | | | | |
| Leucine | | | ●■ | | | | |
| Lysine | | | ●■ | | | | |
| Methionine | | | ■ | | | | ●■ |
| 1-Methylhistidine | | | | | | | |
| 3-Methylhistidine | | | | ●■ | | | |
| Phenylalanine | | | ●■ | | | | |

TABLE E-continued

Pro-biofilm amino acids and amino acid derivatives that have an effect on microbes and cause an increase in biofilm formation by the microbes while in the absence of an infusion of glycerol.

| | Reduce or Inhibit B Biofilm | Reduce or Inhibit F Biofilm | Promote B Biofilm | Promote F Biofilm | Reduce Both | Promotes Both | Neutral |
|---|---|---|---|---|---|---|---|
| Ornithine | | | ● | | | | ■ |
| Phospho-ethanolamine* | | | | | | | |
| Phosphoserine | | | | | | | ■ |
| Proline | | | ● | | | | ■ |
| Serine | | | ● | | | | |
| Taurine | | | ● | | | | |
| Threnonine | | | ● | | | | |
| Tryptophan | | | ● | | | | |
| Tyrosine | | | | | | | ● |
| Valine | | | | ● | | | |

TABLE F

Anti-biofilm amino acids and amino acid derivatives that cause microbes to cease biofilm formation and induce biofilm destruction while in the presence of a sufficient concentration of glycerol

| | Reduce or Inhibit B Biofilm | Reduce or Inhibit F Biofilm | Promote B Biofilm | Promote F Biofilm | Reduce Both | Promotes Both | Neutral |
|---|---|---|---|---|---|---|---|
| Alanine | | | | | | | ■ |
| Beta-Alanine | ■ | | | | | | ● |
| 2 Aminoadipic Acid | ●■ | | | | | | |
| 2 Aminobutyric Acid | | | | | | | ●■ |
| Arginine | | | | | | | |
| Asparagine | | | | | | | ● |
| Aspartic Acid | ●●■■ | ●●■■ | | | ●●■■ | | |
| Citrulline | | | | | | | |
| Cystathionine | ● | | | | | | ■ |
| Cysteine | ●●■■ | ●●■■ | | | ●●■■ | | |
| Ethanolamine* | | ■ | | | | | ● |
| Glutamine | | | | | | | ●■ |
| Glutamic Acid | ●●■■ | ●●■■ | | | ●●■■ | | |
| Glycine | | | | | | | |
| Histidine | | | | | | | ●■ |
| Homocysteine | | ●■ | | | | | |
| Hydroxyproline | ●■ | ■ | | | | | |
| Isoleucine | | | | | | | |
| Leucine | | | | | | | |
| Lysine | | | | | | | |
| Methionine | | | | | | | ● |
| 1-Methylhistidine | | | | | | | ●■ |
| 3-Methylhistidine | ● | | | | | | |
| Phenylalanine | | | | | | | |
| Ornithine | | | | | | | ■ |
| Phospho-ethanolamine* | ●■ | | | | | | |
| Phosphoserine | ● | | ● | | | | ■ |
| Proline | ● | | | | | | ■ |
| Serine | | | ● | | | | |
| Taurine | | | | | | | |
| Threnonine | | | | | | | |
| Tryptophan | | | ● | | | | |
| Tyrosine | | | | | | | ● |
| Valine | ● | | | | | | |

All of the 32 amino acids and the 2 amino acid derivatives were examined at concentrations of 0.1 to 5.0% in their effect on biofilm.

The presence of a sufficient concentration of glycerol sensitizes microbes to the anti-biofilm amino acids and amino acid derivatives in their ability to affect the biofilm-forming microbes to inhibit biofilm formation and can also cause the microbes to actively or by default, cause destruction of pre-formed biofilm.

The presence of glycerol at an appropriate concentration causes biofilm producing microbes to become insensitive to pro-biofilm amino acids and amino acid derivatives.

The presence of an appropriate concentration of glycerol blocked the effect of pro-biofilm amino acids on biofilm-forming microbes. This allows the effect of the competing anti-biofilm amino acids and amino acid derivatives to become dominant over the pro-biofilm amino acids.

The 3% glycerol in the first infusion discussed in Example 1 enabled the chronically infected ulcer that was caused by a bacterial infection and that had been protected by the presence of bacterial biofilm from IV antibiotics and her immune system to heal.

From a practical clinical point of view, the best method to estimate the appropriate concentration of glycerol that needs to be infused for a particular infection is trial and error while evaluating clinical efficacy. The amount of glycerol that was infused into the plasma of the treated patient who weighed 70 kg was approximately 2.4 to 3.0 grams per hour. This would translate, for example, to approximately:

1.7 to 2.1 g/h glycerol into a 50 kg adult, depending on lean body weight
2.0 to 2.6 g/h glycerol into a 60 kg adult
2.4 to 3.0 g/h glycerol into a 70 kg adult
2.7 to 3.4 g/h glycerol into an 80 kg adult
3.0 to 4.0 g/h glycerol into a 90 kg adult
3.4 to 4.3 g/h glycerol into a 100 kg adult, etc.

Glycerol can also be given systemically via the G.I. tract, but more importantly, by absorption through a mucus membrane. Giving it P.O. for absorption through the G.I. tract causes nausea and also exposes the glycerol to a first pass through the liver. This would cause much of the glycerol to be metabolized before it could reach the source of infection. The best places for mucus membrane transfer of glycerol to venous blood would be in the vagina and the distal rectum. In these locations, the venous blood is not exposed to the first pass through the liver but enters the systemic venous system, which goes straight to the heart.

Additionally, the application of glycerol onto a superficial skin lesion in the presence of an antimicrobial can treat a non-healing skin lesion caused by a biofilm-forming organism (see above).

The glycerol in the venous return to the heart is diluted by the venous pool in the vena cava. It is further diluted in the arterial output from the heart. For this reason, one can see that the concentration of glycerol that reaches the site of infection is less than what is initially infused at the site of venous infusion. It should be noted that there is a wide range between an effective concentration of glycerol and a toxic concentration of glycerol. Testing arterial blood samples in order to estimate the concentration of glycerol to be administered would be very impractical and impossible in most situations. Clinicians, therefore, would have to depend on estimating the venous concentration of glycerol that they would expect to be functional in destroying biofilm.

In the natural state of plasma, the presence of the usual concentration of glycerol in the range of 0.05 to 0.1 mmol/L (0.00046% to 0.00092%) has no effect on microbes. By administering glycerol into the plasma of an animal at a rate similar to that suggested above, the plasma glycerol concentration is artificially increased to a non-natural therapeutically acceptable level that will be effective in aiding the destruction of biofilm and reduce formation of biofilm.

The new and significant changes that occur in the physiology of the infecting biofilm forming microbes while in the presence of a therapeutic concentration of glycerol aids in their propensity to stop making new biofilm and either actively or by a lack of support cause destruction of already made biofilm while also in the presence of antibiofilm amino acids and/or antibiofilm amino acid derivatives.

Over the eons, the concentration of Glycerol in the plasma of animals has had no effect on infecting microbes. An elevated concentration of Glycerol has a direct effect on the infecting microbe, which is independent of plasma amino acids. This would be a direct connection between Glycerol and the infecting microbe with a direct effect of the Glycerol on the physiology of the microbe rather than on the amino acids themselves.

While in the presence of a therapeutic concentration of glycerol these microbes become sensitized to the presence of antibiofilm amino acids and antibiofilm amino acids which results in the annihilation of the biofilm.

The new absence of sensitivity in the microbes to pro-biofilm amino acids and amino acid derivatives allows the less dominant antibiofilm amino acids and amino acid derivatives to influence the infecting microbes.

The infusion of glycerol into plasma reduced the usual support of plasma pro-biofilm amino acids and pro-biofilm amino acid derivatives in the production of biofilm. These pro-biofilm amino acids and amino acid derivatives made a welcome environment to infectious biofilm-forming microbes over the eons. For the first time, the help of these pro-biofilm amino acids and pro-biofilm amino acid derivatives became unavailable to the invading biofilm-forming microbes when the concentration of glycerol in the plasma was raised from 0.00048-00096% in systemic venous plasma to approximately 0.04% in systemic venous plasma by the infusion of glycerol at a rate of 0.8 g/L/hour into venous blood or 0.4 g/L/hour into plasma or 0.04 g/100 ml/hour into arterial plasma. This rate of glycerol infusion into plasma has been found to be non-toxic to humans though it could be potentially harmful to patients with poor kidney function and some other rare metabolic disorders that would be familiar to the treating clinician and can be easily dealt with by reducing the rate of glycerol infusion. Overall, this infusion can be regarded as a safe treatment.

There are some amino acids and amino acid derivatives that have the dual effect of being either pro-biofilm effect or antibiofilm molecules. The presence of a therapeutic concentration of glycerol suppresses the pro-biofilm effect and enhances the antibiofilm effect in the infecting microbes.

Besides the advantage that biofilm affords to infections caused by pathogenic biofilm-producing microbes from assault by the immune system and administered antimicrobials, the biofilm offers an environment conducive to the development of genetic resistance to antimicrobials.

Example 3: Patient Study

The inventor had a tear on the skin in the upper portion of his lower leg after the removal of adhesive tape in the area. The lesion area measured 1.5×0.5 cm. For 6 weeks, the skin did not cover any of this denuded area. It was treated by wound care specialists twice during this period, the patient received IV. antibiotics for sepsis. Eventually, he received containers of 50% sterilized glycerol. 2×2 gauze patches that had glycerol applied to them were laid over the lesion and an oral antibiotic was begun. Three days after application, one could see the skin beginning to encroach on the lesion with an isthmus of skin crossing the lesion at the center. Seven days after application, the lesion was again examined and skin covered approximately 90% of the lesion area with small areas of non-coverage at the poles. When examined again 3 days later, the lesion was entirely covered by skin and the area was reduced in size; the oral antibiotic was discontinued. Twelve days after application, the area looked slim and had some scarring. This shows that the antibiotic gained access to the bacterium in the superficial lesion from within the body, whereas the glycerol gained access to the bacteria from the surface of the superficial bed of the lesion. This would indicate that lesions involving skin can be treated with oral antibiotics or IV. antibiotics and a topical application of glycerol. It indicates that antibiofilm amino acids and amino acid derivatives gained access to the infecting bacteria from nearby plasma.

Stated in different ways, the administration of the glycerol only composition has the following advantages:

In the presence of a sufficient nontoxic concentration of glycerol there is an effect on the infecting biofilm-producing microbes which cause them to become insensitive to pro-biofilm amino acids and amino acid derivatives in plasma.

The presence of a sufficient nontoxic plasma concentration of glycerol has an effect on the infecting biofilm-producing microbes which causes them to become sensitized to a lower concentration of antibiofilm amino acids and antibiofilm amino acid derivatives.

The lower concentration of anti-biofilm amino acids and amino acid derivatives that is enabled by a sufficiently elevated level of Glycerol at the site of the infection causes microbes to cease making new biofilm and causes preformed biofilm to disintegrate.

The presence of a therapeutic plasma concentration of glycerol enables a biofilm-producing infection in an animal, including a human, to become more sensitive to an attack by the immune system and an administered antimicrobial.

By aiding in the prevention and destruction of biofilm, the presence of a therapeutic plasma concentration of glycerol prevents the spread of new biofilm communities in the body.

In the treatment of plants, water, and infected surfaces, the administration of glycerol and antibiofilm amino acids and/or amino acid derivatives along with an antimicrobial and/or a sterilizing agent can treat microbial infections and contaminations.

Glycerol, by aiding the prevention and destruction of biofilm, will aid in the prevention and spread of antimicrobial resistance.

The effect of glycerol in treating biofilm-forming protozoa and viruses will aid anti-biofilm amino acids and amino acid derivatives plus an anti-microbial and/or a sterilizing agent in the treatment of these disorders.

A therapeutic concentration of Glycerol can aid antimicrobials and the immune system in killing the fungi and bacteria in hybrid infections.

A superficial non-healing skin lesion caused by biofilm-forming microbes can be successfully treated by the superficial application of glycerol to the wound and the use of an antimicrobial.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference.

What is claimed is:

1. A method of desensitizing microbes to pro-biofilm amino acids and amino acid derivatives in plasma comprising administering a solution comprising a sufficient, nontoxic concentration of glycerol, wherein glycerol is the sole therapeutic agent.

2. The method of claim 1, wherein the step of administering comprises administering to a wound the solution.

3. The method of claim 1, wherein the step of administering comprises administering the solution vaginally, rectally, orally, intravenously, intra-arterially, intracavernously, intrathecally, and/or topically.

4. The method of claim 1, wherein 1.7 to 4.3 g/h of glycerol are administered intravenously and/or intra-arterially.

5. The method of claim 1, further comprising the step of administering at least one antimicrobial.

* * * * *